(12) United States Patent
Sano et al.

(10) Patent No.: US 11,272,894 B2
(45) Date of Patent: Mar. 15, 2022

(54) X-RAY IMAGING DEVICE

(71) Applicant: Shimadzu Corporation, Kyoto (JP)

(72) Inventors: Satoshi Sano, Kyoto (JP); Koichi Tanabe, Kyoto (JP); Yukihisa Wada, Kyoto (JP); Satoshi Tokuda, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/041,986

(22) PCT Filed: Jan. 22, 2019

(86) PCT No.: PCT/JP2019/001924
§ 371 (c)(1),
(2) Date: Sep. 25, 2020

(87) PCT Pub. No.: WO2019/239624
PCT Pub. Date: Dec. 19, 2019

(65) Prior Publication Data
US 2021/0137476 A1    May 13, 2021

(30) Foreign Application Priority Data
Jun. 15, 2018   (JP) .............................. JP2018-114211

(51) Int. Cl.
*G01N 23/041*   (2018.01)
*G01N 23/046*   (2018.01)
*A61B 6/00*    (2006.01)
*A61B 6/03*    (2006.01)
*A61B 6/04*    (2006.01)

(52) U.S. Cl.
CPC .............. *A61B 6/484* (2013.01); *A61B 6/032* (2013.01); *A61B 6/0492* (2013.01); *A61B 6/4035* (2013.01); *A61B 6/582* (2013.01)

(58) Field of Classification Search
CPC ..... A61B 6/484; A61B 6/4035; A61B 6/0492; A61B 6/582; A61B 6/032; A61B 6/5235; G01N 23/041; G01N 2223/401; G01N 23/046
See application file for complete search history.

(56) References Cited

U.S. PATENT DOCUMENTS

2018/0356355 A1   12/2018  Momose et al.
2021/0364453 A1*  11/2021  Sano ................. G01N 23/041

FOREIGN PATENT DOCUMENTS

JP         2017-044603 A      3/2017

OTHER PUBLICATIONS

Written Opinion of the International Searching Authority dated Apr. 16, 2019 for PCT application No. PCT/JP2019/001924, submitted with a machine translation.

* cited by examiner

*Primary Examiner* — Don K Wong
(74) *Attorney, Agent, or Firm* — Muir Patent Law, PLLC

(57) ABSTRACT

The X-ray imaging device (100) is provided with an imaging system (CS) including an X-ray source (1), a detector (5), and a plurality of gratings, a moving mechanism (8), a position information acquisition unit (7a), and an image processing unit (6) for generating a phase-contrast image (16) in a tomographic plane by acquiring a phase distribution in a tomographic plane (40) based on a plurality of X-ray images (10) and the acquired tomographic position (z+jd).

13 Claims, 15 Drawing Sheets

First Embodiment

First Embodiment

FIG. 10
(Acquisition of phase information of Moire fringe: M=4)
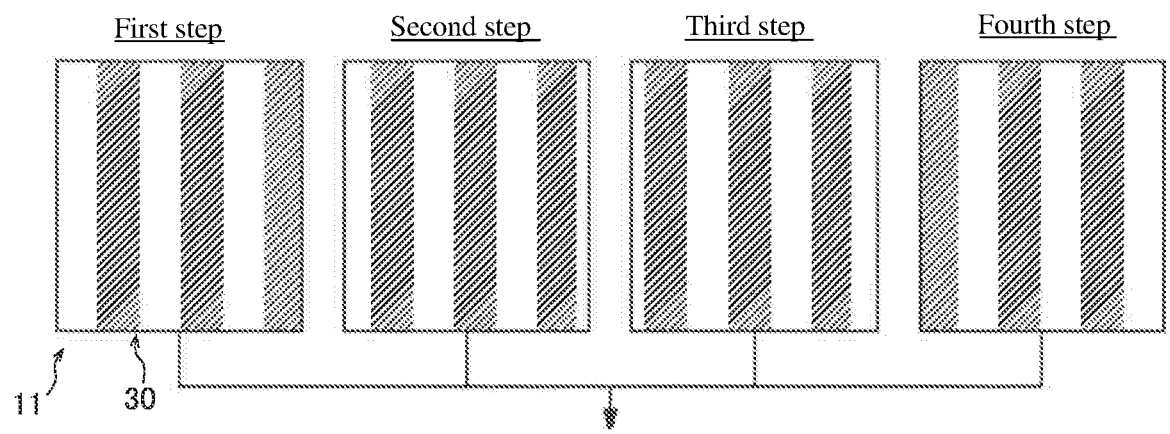
Phase information of the Moire fringe
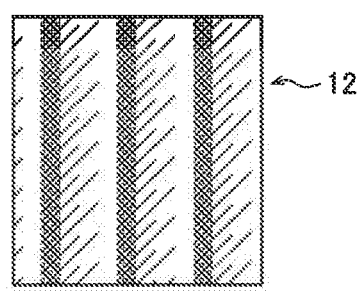

(X-ray image and position information after coordinate transformation)

First Embodiment

First Embodiment

Second Embodiment

Third Embodiment

Fourth Embodiment

Fourth Embodiment

Fourth Embodiment

Fourth Embodiment

X-RAY IMAGING DEVICE

TECHNICAL FIELD

The present invention relates to an X-ray imaging device, and particularly to an X-ray imaging device for imaging a subject while moving the subject.

BACKGROUND ART

Conventionally, an X-ray imaging device for imaging a subject while moving the subject is known. Such an X-ray imaging device is disclosed, for example, in Japanese Unexamined Patent Application Publication No. 2017-44603.

In recent years, there is a need for an X-ray imaging device for substances, such as, e.g., biological soft tissues and polymer materials. Since a biological soft tissue, a polymer material, or the like is small in the X-ray absorption, it is difficult to capture a high-contrast image by conventional X-ray imaging in which an image is formed based on the contrast of the X-ray absorption amount since the X-ray absorption is low. As a technique for imaging a biological soft tissue, a polymer material, or the like that absorbs less X-rays, a technique called a fringe scanning method for generating a phase-contrast image is known. The fringe scanning method is a method in which imaging is performed while translating one of a plurality of gratings at a predetermined pitch, the phase distribution is acquired based on the X-ray intensity detected for each pixel, and an image is formed based on the acquired phase distribution. In this specification, a phase-contrast image means an image in which contrast is generated using a phase distribution in an X-ray image.

A conventional fringe scanning method has a disadvantage that a visual field size is limited to a size of a grating because the imaging is performed while relatively moving the grating in a state in which the relative position between a subject and an imaging system is fixed. Therefore, the X-ray imaging device disclosed in Japanese Unexamined Patent Application Publication No. 2017-44603 is configured to perform imaging while moving a subject.

Specifically, the X-ray imaging device disclosed in Japanese Unexamined Patent Application Publication No. 2017-44603 is provided with an X-ray source, a grating group including a first grating, a second grating, and a third grating, a detection unit, a transfer unit for moving a subject, and an image operation unit. The X-ray imaging device disclosed in Japanese Unexamined Patent Application Publication No. 2017-44603 captures a plurality of X-ray images while moving a subject in a period direction of a Moire fringe by the transfer unit in a state in which the Moire fringe is generated on a detection surface by a plurality of gratings irradiated with X-rays. Then, the image operation unit generates a phase-contrast image of each of an absorption image, a phase differential image, and a dark-field image from the plurality of X-ray images acquired. Note that an absorption image is an image generated based on the attenuation of X-rays caused when the X-rays pass through a subject. Also note that a phase differential image is an image generated based on a phase deviation of X-rays caused when X-rays pass through a subject. A dark-field image is a visibility image acquired by a change in visibility based on the small-angle scattering of an object. The dark-field image is also called a small-angle scattering image. "visibility" refers to sharpness.

PRIOR ART DOCUMENT

Patent Document

Patent Document 1: Japanese Unexamined Patent Application Publication No. 2017-44603

SUMMARY OF THE INVENTION

Problems to be Solved by the Invention

However, in Japanese Unexamined Patent Application Publication No. 2017-44603, when a thickness of a subject in an optical axis direction of X-rays is increased, there is a disadvantage that in the generated phase-contrast image, the internal structure to be imaged in the subject is blurred (the contour of the image becomes unclear). That is, in cases where a thickness of a subject is large, even in the same site of the subject, for example, since the difference in the incidence angle of X-rays is large between the front side and the rear side in the optical axis direction, so that X-rays that have passed through the front side and X-rays that have passed through the rear sides are detected at different positions of the detector. Consequently, since the deviation of the detection position due to the thickness of the subject is reflected in the phase distribution, the image of the internal structure to be imaged is blurred, resulting in a decrease in visibility. Therefore, even in a subject having a large thickness, it is desired to be able to suppress a decrease in visibility of an internal structure to be imaged due to blurring.

The present invention has been made to solve the above-mentioned problems, and one object of the present invention is to provide an X-ray imaging device capable of suppressing a decrease in visibility of an internal structure to be imaged even in a subject having a large thickness.

Means for Solving the Problem

In order to achieve the above-described object, an X-ray imaging device according to one aspect of the present invention includes:

an X-ray source;

a detector configured to detect X-rays emitted from the X-ray source;

a plurality of gratings arranged between the X-ray source and the detector, the plurality of gratings including a first grating configured to be irradiated with the X-rays from the X-ray source and a second grating configured to be irradiated with X-rays that have passed through the first grating;

a moving mechanism configured to relatively move an imaging system and a subject in a predetermined direction intersecting with an optical axis direction of the X-rays, the imaging system including the X-ray source, the detector, and the plurality of gratings;

a position information acquisition unit configured to acquire a tomographic position of a tomographic plane to be imaged in the optical axis direction; and an image processing unit configured to acquire a phase distribution in the tomographic plane based on a plurality of X-ray images acquired by imaging the subject at a plurality of relative positions between the imaging system and the subject in the predetermined direction and on the acquired tomographic position, thereby generating a phase-contrast image in the tomographic plan.

Note that the tomographic position in this specification is a concept indicating a position of a tomographic plane in an optical direction. The tomographic position may be rephrased as a distance from an X-ray source in an optical direction.

In the X-ray imaging device according to one aspect of the present invention, as described above, it is provided with a position information acquisition unit configured to acquire a tomographic position of a tomographic plane to be imaged in the optical axis direction; and an image processing unit configured to acquire a phase distribution in the tomographic plane based on a plurality of X-ray images acquired by imaging the subject at a plurality of relative positions between the imaging system and the subject in the predetermined direction and on the acquired tomographic position, thereby generating a phase-contrast image in the tomographic plan. With this, the position (tomographic position) of the tomographic plane in the subject in the optical axis direction in which the internal structure to be imaged is present can be acquired by the position information acquisition unit. Since the incidence angle of the X-rays with respect to the point on the tomographic plane is determined by the relative position between the imaging system and the subject, the position of the point on the tomographic plane in each X-ray image can be identified by the information of the tomographic position and the relative position when the X-ray image is captured. This allows the image processing unit to acquire the phase distribution in a particular tomographic plane indicated by the tomographic position based on the acquired tomographic position information and the respective X-ray images at the plurality of relative positions. Consequently, from the phase distribution in the tomographic plane at the tomographic position acquired by the position information acquisition unit, a phase-contrast image (tomographic image) in which blurring of an image is suppressed for the internal structure contained in the tomographic plane can be acquired. As a result, even in the case of a subject having a large thickness, it is possible to suppress the deterioration in the visibility of the internal structure.

Note that when the tomographic position to be acquired by the position information acquisition unit is changed, the internal structure contained in the tomographic plane indicated by the tomographic position after the change can be visually recognized by the phase-contrast image (tomographic image) in which blurring of an image is suppressed. Therefore, according to the above-described configuration, depending on the user's desired tomographic position to be imaged (e.g., the tomographic plane on the front side or the tomographic plane on the back side of the subject having a large thickness), it is possible to acquire a highly visible phase-contrast image (tomographic image) in any tomographic plane. Since the decrease in visibility due to blurring of an image gives a larger impact as the internal structure to be imaged becomes finer, the above-described configuration is particularly useful when a detailed check of a fine structure or an internal structure is desired.

In the X-ray imaging device according to the aforementioned one aspect of the present invention, preferably, the image processing unit is configured to perform a coordinate transformation for special coordinates in each of the X-ray images into ones defined in a transformed coordinate system on the tomographic plane, based on 1) the relative position at the time of capturing each X-ray image and 2) the acquired tomographic position, thereby acquiring a phase distribution in the tomographic plane based on pixel values of each of the X-ray images defined from the transformed coordinate system. As described above, the geometric relative position between the X-ray source, the subject, and the detector (i.e., the positional coordinate in the X-ray image) is determined from the relative position between the imaging system and the subject in the predetermined direction and the tomographic position in the optical axis direction. Therefore, by performing a coordinate transformation using the geometric relation so that the same position of the subject in the tomographic plane matches each other on the X-ray images, the phase distribution in the tomographic plane can be easily acquired.

In the X-ray imaging device according to the aforementioned one aspect of the present invention, preferably, the position information acquisition unit acquires a deviation of the tomographic position relative to a reference position in the optical axis direction, and the image processing unit is configured to acquire a phase distribution in the tomographic plane based on a deviation between the reference position and the tomographic position relative to the reference position in the optical axis direction and the relative position between the imaging system and the subject in the predetermined direction. With this configuration, for example, at the time of imaging, by arranging a predetermined position such as the center of the subject at a preset reference position, the tomographic position of the subject in the optical axis direction can be treated as a distance (deviation) from the reference position. Consequently, the tomographic position to be imaged in the subject can be easily specified, and the desired phase-contrast tomographic image can be easily acquired.

In this case, preferably, the image processing unit is configured to: generate position calibration data that associate a movement amount by the moving mechanism with a change amount of the relative position in the X-ray image, based on a plurality of position calibration images captured by imaging a marker arranged at the reference position in the optical axis direction at a plurality of relative positions in the predetermined directions; and acquire a phase distribution in the tomographic plane using the position calibration data acquired at the reference position. In order to suppress the blurring of the image in the phase-contrast image, it is important to specify the relative position between the imaging system and the subject with high accuracy. Therefore, by generating the position calibration data with the above-described configuration, it is possible to accurately acquire the actual position change of the point (marker) on the tomographic plane passing through the reference position on each X-ray image. Since the position of the point on the tomographic plane passing through the reference position can be accurately grasped, the position coordinate on any tomographic plane can be accurately grasped by the position calibration data at the reference position and the deviation from the reference position without generating the position calibration data at each tomographic position. Consequently, by simply generating the position calibration data of the reference position, the phase distribution at any tomographic plane acquired by the position information acquisition unit can be acquired with high accuracy.

In the above-mentioned configuration for generating the position calibration data, preferably, the moving mechanism is configured to relatively move the imaging system and the subject to the same relative position as each relative position between the imaging system and the marker at the time of generating the position calibration data when imaging the subject. With this configuration, it is possible to generate the phase-contrast image (tomographic image) of the tomographic plane based on the X-ray image captured at the same relative position as when generating the position calibration data. Therefore, the error factor of the position calibration data is eliminated as much as possible, so it is possible to identify the relative position between the imaging system and the subject in each X-ray image more accurately.

In the X-ray imaging device according to the aforementioned one aspect of the present invention, preferably, the position information acquisition unit acquires the tomographic positions of the plurality of tomographic planes shifted in the optical axis direction, and the image processing unit is configured to acquire the phase-contrast image in each tomographic plane and generate three-dimensional data of the subject based on the acquired phase-contrast image. With this configuration, from the plurality of tomographic images, it is possible to acquire the three-dimensional data depicting the distribution of the internal structure in the subject in the optical axis direction. Further, since the blurring of an image can be suppressed for each tomographic image constituting the three-dimensional data, the three-dimensional structure in the subject can be grasped more precisely.

In the X-ray imaging device according to the aforementioned one aspect of the present invention, preferably, the moving mechanism is configured to continuously and relatively move the imaging system and the subject when imaging the subject, and the image processing unit is configured to generate the phase-contrast image based on each of the X-ray images acquired continuously. With this configuration, even when capturing the X-ray images at a plurality of relative positions, it is possible to complete the imaging in a short time, so it is possible to quickly acquire the phase-contrast image of the desired tomographic position. Further, by completing the imaging in a short time, it is possible to suppress the effects such as deviation of the relative position due to thermal variations during the imaging of the respective X-ray images.

In the X-ray imaging device according to the aforementioned one aspect of the present invention, preferably, the moving mechanism is configured to move the subject to the plurality of relative positions by repeatedly performing a relative movement of the imaging system and the subject and stopping of the relative movement thereof when imaging the subject, and the image processing unit is configured to generate the phase-contrast image based on the respective X-ray images acquired at the plurality of relative positions. With this configuration, since it is possible to capture each X-ray image in a stationary state, it is possible to capture the X-ray image by suppressing the deviation of the relative position or blurring of the image as much as possible.

In the X-ray imaging device according to the aforementioned one aspect of the present invention, preferably, the moving mechanism is configured to move the subject with respect to the imaging system in the predetermined direction. With this configuration, unlike the case in which the entire imaging system including the X-ray source, each grating, and the detector is moved, it is sufficient to move only the subject, so that it is possible to simplify and miniaturize the moving mechanism and it is possible to easily secure the position accuracy at the time of the movement.

In the X-ray imaging device according to the aforementioned one aspect of the present invention, preferably, the detector includes a first detection region for detecting X-rays arrived by passing through the first grating and a second detection region for detecting X-rays arrived without passing through the first grating, the moving mechanism relatively moves the imaging system and the subject so that the subject is arranged in the first detection region and the second detection region, respectively, and the image processing unit is configured to generate the phase-contrast image based on a plurality of first images captured in the first detection region and generate an absorption image of the subject based on a plurality of second images captured in the second detection region. With this configuration, although it is an imaging system provided with a grating between the X-ray source and the detector, it is possible to generate not only the phase-contrast image using the grating but also the absorption image not interposing the grating. The X-rays reaching the second detection region reaches the detector without passing through the grating, the attenuation of the X-rays by the grating, in particular, the attenuation of the low-energy side X-rays can be suppressed. As a result, the contrast of the absorption image generated by the X-rays reaching the second detection region can be improved as compared with the absorption image generated by the X-rays reaching the first detection region.

In this case, preferably, the image processing unit is configured to generate a composite image in which the phase-contrast image and the absorption image in the same tomographic plane are composed. With this configuration, it is possible to acquire a composite image in which the high-contrast absorption image generated by the X-rays detected in the second detection region and the phase-contrast image in the same tomographic plane are composed. Consequently, by treating as the tomographic image of a particular tomographic plane, it is possible to acquire a high-contrast tomographic image (composite image) containing the absorption (attenuation) distribution and the phase distribution information in the tomographic plane while suppressing blurring of the image.

In the above-mentioned configuration for generating a composite image, preferably, the position information acquisition unit acquires the tomographic positions of the plurality of tomographic planes shifted in the optical axis direction, and the image processing unit is configured to acquire the phase-contrast image and the absorption image in each tomographic plane to generate three-dimensional data of the phase-contrast image and three-dimensional data of the absorption image and generate three-dimensional composite data in which the respective three-dimensional data is composed. With this configuration, from the phase-contrast image and the absorption image in each of the plurality of tomographic planes, it is possible to acquire the three-dimensional data depicting the distribution of the internal structure in the subject in the optical axis direction. The phase-contrast image is suitable for depicting the border portion and the fine structural change in the internal structure of the subject that cause refraction and scattering of X-rays, and the absorption image is suitable for depicting the solid portion that causes attenuation of X-rays. Therefore, by acquiring the three-dimensional composite data in which the depictable portions of the phase-contrast image and the absorption image are composed, the three-dimensional structure in the subject can be depicted more accurately.

In the X-ray imaging device according to the aforementioned one aspect of the present invention, preferably, the plurality of gratings further includes a third grating arranged between the X-ray source and the first grating. By configuring as described above, the coherence of the X-rays emitted from the X-ray source can be enhanced by the third grating. As a result, even if the focal diameter of the X-ray source is large, the self-image of the first grating can be formed, so that the flexibility in selecting the X-ray source can be improved.

Effects of the Invention

According to the present invention, as described above, even in the case of a subject having a large thickness, it is possible to suppress a decrease in visibility of an internal structure of the subject to be imaged.

BRIEF DESCRIPTION OF THE DRAWINGS

FIG. 10 is a schematic diagram for explaining a method of acquiring phase information of a Moire fringe.

EMBODIMENTS FOR CARRYING OUT THE INVENTION

Hereinafter, some embodiments in which the present invention is embodied will be described with reference to the attached drawings.

First Embodiment

Referring to FIG. 1 to FIG. 15, an X-ray imaging device 100 according to a first embodiment will be described.

(Configuration of X-Ray Imaging Device)

First, referring to FIG. 1 to FIG. 3, the configuration of the X-ray imaging device 100 according to the first embodiment will be described.

Figure 1:
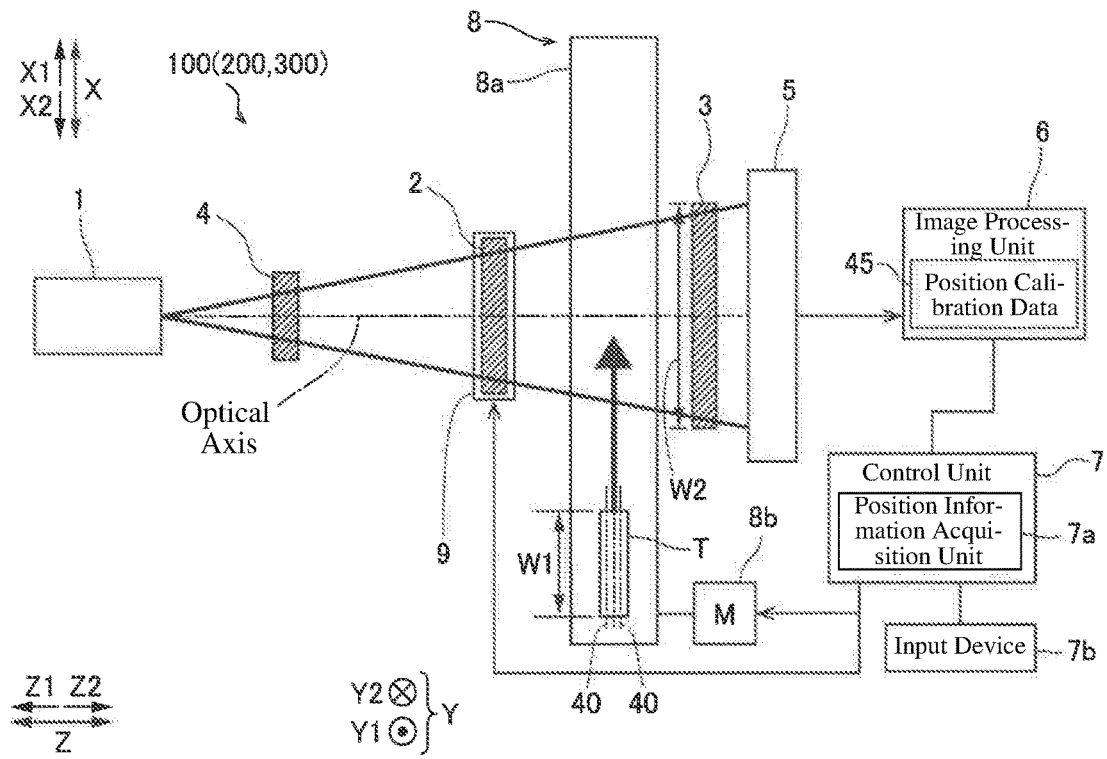
FIG. 1 is a schematic diagram showing the overall configuration of an X-ray imaging device.

As shown in FIG. 1, the X-ray imaging device 100 is a device for imaging an internal structure of a subject T using a Talbot effect. The X-ray imaging device 100 can be used to image an inside of a subject T as an object, for example, in a non-destructive inspection application.

The X-ray imaging device 100 is provided with an X-ray source 1, a first grating 2, a second grating 3, a third grating 4, a detector 5, an image processing unit 6, a control unit 7, a moving mechanism 8, and a grating moving mechanism 9. The X-ray source 1, the first grating 2, the second grating 3, the third grating 4, and the detector 5 constitute an imaging system CS of the X-ray imaging device 100.

Hereinafter, the direction of the optical axis (the center axis of the light flux of the X-rays) of the X-rays emitted from the X-ray source 1 is defined as a Z-direction, the direction from the X-ray source 1 toward the first grating 2 in the Z-direction is defined as a Z2-direction, and the direction opposite thereto is defined as a Z1-direction. Two directions orthogonal to each other in a plane orthogonal to the Z-direction are defined as an X-direction and a Y-direction, respectively. Although not particularly limited, hereinafter, for convenience, the Y-direction is defined as an up-down direction (vertical direction), and the X-direction is defined as a horizontal direction. FIG. 1 is a view of the X-ray imaging device 100 as viewed in the Y-direction. Note that, in the first embodiment, an example is shown in which the size W1 of the subject T to be imaged in the X-direction is smaller than the width W2 of the second grating 3 in the X-direction.

The X-ray source 1 generates X-rays when a high voltage is applied. The X-ray source 1 is configured to emit the generated X-rays in the Z2-direction (toward the detector 5). The X-ray source 1 is arranged so as to face the detector 5. The X-ray source 1 is arranged, for example, at a position where the optical axis of the X-rays from the X-ray source 1 passes through the center of the detection surface of the detector 5. The optical axis direction coincides with the normal direction to the detection surface of the detector 5.

In the first embodiment, the X-ray imaging device 100 is provided with three or more (a plurality of) gratings, i.e., the first grating 2, the second grating 3, and the third grating 4. The first grating 2 is arranged between the X-ray source 1 and the detector 5 and is irradiated with the X-rays from the X-ray source 1. The first grating 2 is provided to form a self-image of the first grating 2 by a Talbot effect. When coherent X-rays pass through a grating in which slits are formed, an image (self-image) of the grating is formed at a predetermined distance (Talbot distance) away from the grating. This is called a Talbot effect.

The second grating 3 is arranged between the first grating 2 and the detector 5 and is irradiated with the X-rays that have passed through the first grating 2. The second grating 3 is arranged at a position away from the first grating 2 by a predetermined Talbot distance. The second grating 3 interferes with the self-image of the first grating 2 to form a Moire fringe 30 (see FIG. 4).

The third grating 4 is arranged between the X-ray source 1 and the first grating 2 and is irradiated with the X-rays from the X-ray source 1. The third grating 4 forms an array of micro light sources smaller than the focal diameter of the X-ray source 1 by a plurality of respective X-ray transmission regions. In addition to the first grating 2 and the second grating 3, a so-called Talbot-Lau interferometer is constructed by providing the third grating 4.

The detector 5 detects the X-rays emitted from the X-ray source 1. The detector 5 is configured to convert the detected X-rays to an electric signal and read the converted electric signal as an image signal. The detector 5 is, for example, an FPD (Flat Panel Detector). The detector 5 is provided with a plurality of pixels composed of a plurality of conversion elements (not shown) and pixel electrodes (not shown) arranged on the conversion elements. The plurality of pixels is arrayed in an array in the X-direction and the Y-direction at a predetermined period (pixel pitch). The detector 5 is configured to output the acquired image signal to the image processing unit 6.

The image processing unit 6 is configured to generate a phase-contrast image 16 (see FIG. 13) based on the image signal outputted from the detector 5. The image processing unit 6 includes a processor, such as, e.g., a GPU (Graphics Processing Unit) and an FPGA (Field-Programmable Gate Array) configured for image processing.

The control unit 7 controls the imaging operation of the X-ray imaging device 100. Specifically, the control unit 7 is configured to control the moving mechanism 8 to relatively move the imaging system CS and the subject T. The control unit 7 is configured to control the grating moving mechanism 9 to move the first grating 2. The control unit 7 is configured to cause a Moire fringe 30 (see FIG. 4) to occur on the detection surface of the detector 5 by controlling the grating moving mechanism 9 to adjust the position of the first grating 2. The control unit 7 includes, for example, a processor, such as, e.g., a CPU (Central Processing Unit), and a storage unit, such as, e.g., a ROM (Read Only Memory) and a RAM (Random Access Memory).

In the first embodiment, the control unit 7 includes a position information acquisition unit 7a. The position information acquisition unit 7a is configured to acquire a tomographic position of the tomographic plane 40 to be imaged in the optical axis direction. The position information acquisition unit 7a can be implemented in software, for example, by a program that make the CPU operate as the position information acquisition unit. The position information acquisition unit 7a acquires the tomographic position inputted by a user via an input device 7b, such as, e.g., a keyboard provided, in the control unit 7. The position information acquisition unit 7a can acquire the tomographic position by reading out the information of a tomographic position stored in advance in a storage unit provided in the control unit 7, an external storage medium, or the like. As will be described later, the X-ray imaging device 100 of the first embodiment can generate a phase-contrast image 16 (tomographic image) at the tomographic plane 40 defined by the acquired tomographic position.

The moving mechanism 8 is configured to relatively move the imaging system CS and the subject T in a predetermined direction intersecting with the optical axis direction of the X-rays. In the first embodiment, the optical axis direction is the Z-direction and the predefined direction is the X-direction perpendicular to the optical axis direction. In addition, the moving mechanism 8 relatively moves the imaging system CS and the subject T in a period direction (X-direction) of the Moire fringe 30 (see FIG. 4) in a plane perpendicular to the optical axis direction. The moving mechanism 8 may be configured to move one or both of the imaging system CS and the subject T. In the first embodiment, the moving mechanism 8 moves the subject T in the X-direction with respect to the imaging system CS. The imaging system CS is fixed at least during the imaging operation except that the first grating 2 is moved by the grating moving mechanism 9. The moving mechanism 8 includes, for example, a belt conveyor 8a or various linear motion mechanisms and a drive source 8b, such as an electric motor. The linear motion mechanism may include a guide mechanism (not shown), such as, e.g., a linear slider, and a conversion mechanism (not shown), such as, e.g., a ball screw mechanism or a rack-pinion mechanism, that converts the power from the drive source 8b into the X-direction motion. By way of example, in the first embodiment, the moving mechanism 8 includes a drive source 8b composed of a stepping motor.

The grating moving mechanism 9 is movably holding the first grating 2. The grating moving mechanism 9 is configured to move the first grating 2 under the control of the control unit 7. Further, the grating moving mechanism 9 is configured to be able to hold the first grating 2 in a state in which the position of the first grating 2 is adjusted to a predetermined position under the control of control unit 7.

(Structure of Each Grating)

Figure 2:
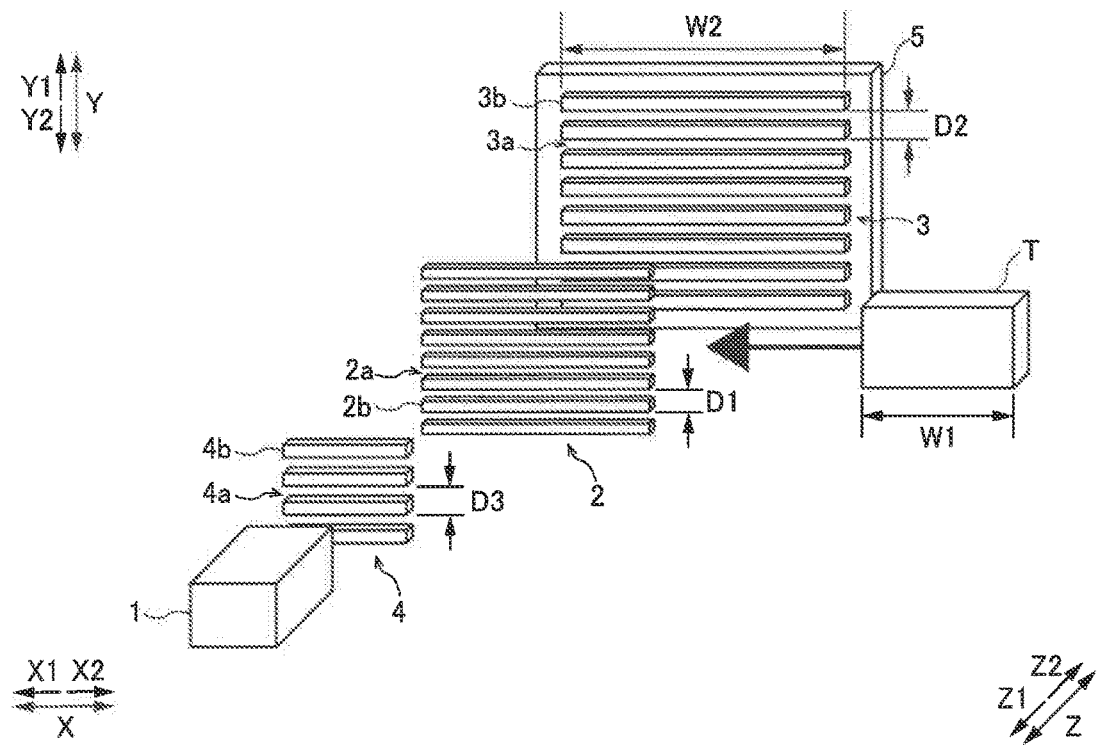
FIG. 2 is a schematic diagram for explaining a plurality of gratings of the X-ray imaging device.

As shown in FIG. 2, the first grating 2 has a plurality of slits 2a and a plurality of X-ray phase change portions 2b. Each slit 2a and each X-ray phase change portion 2b are arranged at a predetermined period (pitch) D1 in the Y-direction. The slit 2a and the X-ray phase change portion 2b are each formed so as to extend linearly. The slit 2a and the X-ray phase change portion 2b are each formed so as to extend in parallel with each other. The first grating 2 is a so-called phase grating, but it may be a so-called absorption grating (provided with an X-ray absorption portion instead of the X-ray phase change portion 2b).

The second grating 3 has a plurality of X-ray transmission portions 3a and a plurality of X-ray absorption portions 3b. The X-ray transmission portion 3a and the X-ray absorption portion 3b are arranged in the Y-direction at a predetermined period (pitch) D2. The X-ray transmission portion 3a and the X-ray absorption portion 3b are each formed so as to extend linearly. The X-ray transmission portion 3a and the X-ray absorption portion 3b are each formed so as to extend in parallel with each other. The second grating 3 is a so-called absorption grating.

The third grating 4 has a plurality of slits 4a and a plurality of X-ray absorption portions 4b arranged at a predetermined period (pitch) D3 in the Y-direction. The slit 4a and the X-ray absorption portion 4b are each formed so as to extend linearly. The slit 4a and the X-ray absorption portion 4b are each formed so as to extend in parallel with each other.

At each grating, the slit and the X-ray transmission portion each allow the transmission of X-rays. The X-ray absorption portion shields X-rays. Further, the X-ray phase change portion changes the phase of the X-rays by the difference in the refractive index between the X-ray phase change portion and the slit.

(Grating Moving Mechanism)

Figure 3:
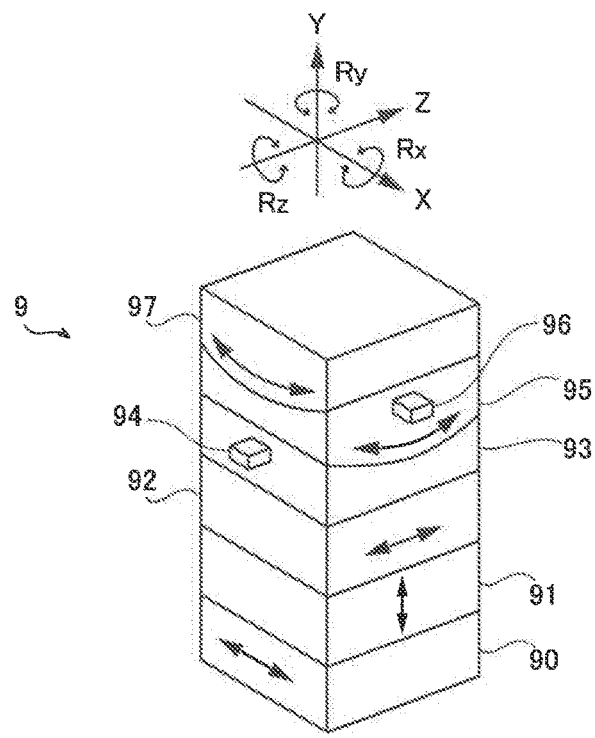
FIG. 3 is a schematic diagram for explaining the configuration of a grating moving mechanism.

In the configuration example of FIG. 3, the grating moving mechanism 9 is a 6-axis moving stage. The grating moving mechanism 9 includes an X-direction linear motion mechanism 90, a Y-direction linear motion mechanism 91, a Z-direction linear motion mechanism 92, a linear motion mechanism connection unit 93, a stage support unit drive unit 94, a stage support unit 95, a stage drive unit 96, and a stage 97. Although not shown, the grating moving mechanism 9 is holding the first grating 2 on the stage 97.

The grating moving mechanism 9 moves the stage 97 (first grating 2) in the X-direction by the X-direction linear motion mechanism 90. The grating moving mechanism 9 moves the stage 97 (first grating 2) in the Y-direction by the Y-direction linear motion mechanism 91. The grating moving mechanism 9 moves the stage 97 (first grating 2) in the Z-direction by the Z-direction linear motion mechanism 92. Each of the linear motion mechanisms includes an electric motor or the like as a drive source. With this, the grating moving mechanism 9 is configured to move the stage 97 (first grating 2) in each of the X-direction, the Y-direction, and the Z-direction.

The stage support unit 95 is supporting the stage 97 from the below (in the Y1-direction). The stage drive unit 96 moves the stage 97 approximately in the X-direction. The stage 97 is formed to have an arcuate bottom surface as a convex curved surface toward the stage support unit 95 and is rotatable about the axis of the Z-direction along the curved surface (rotatable about the Rz-direction) by being moved in the X-direction. The stage support unit drive unit 94 moves the stage support unit 95 approximately in the Z-direction. The stage support unit 95 is formed to have an arcuate bottom surface as a convex curved surface toward the linear motion mechanism connection unit 93 and is rotatable about the axis of the X-direction (in the Rx-direction) by being moved in the Z-direction along the curved surface. Further, the linear motion mechanism connection unit 93 is provided to the X-direction linear motion mechanism 90 so as to be rotatable about the axis of the Y-direction (in the Ry-direction). With this, the grating moving mechanism 9 can rotate the stage 97 (first grating 2) in each direction, i.e., in the Rx-direction, in the Ry-direction, and in the Rz directions.

(Generation of Phase-Contrast Image)

Next, referring to FIG. 4 to FIG. 14, the configuration in which the X-ray imaging device 100 according to the first embodiment generates a phase-contrast image 16 (see FIG. 13) will be described.

Figure 4:
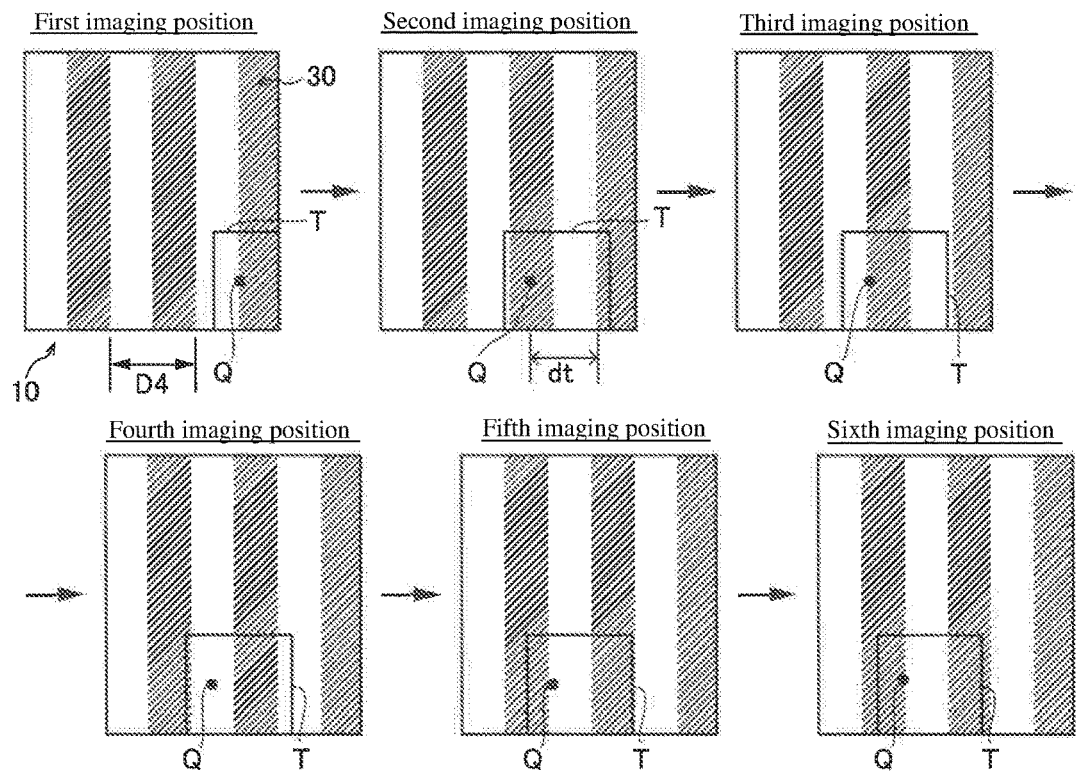
FIG. 4 is a schematic diagram of a plurality of X-ray images captured at respective relative positions.

In the first embodiment, as shown in FIG. 4, the X-ray imaging device 100 captures X-ray images 10 while moving the subject T with respect to the imaging system CS so as to pass through the Moire fringe 30 in a state in which the Moire fringe 30 is generated in advance on the detection surface of the detector 5. The X-ray imaging device 100 generates a phase-contrast image 16 based on the plurality of X-ray images 10 captured at the respective relative positions. In order to generate a phase-contrast image 16, the X-ray imaging device 100 acquires the information of the tomographic position to be imaged, the phase information 12 of the Moire fringe 30 (see FIG. 10), and the information of the relative positions in which the plurality of X-ray images 10 is captured.

In the first embodiment, the image processing unit 6 generates a phase-contrast image 16 (see FIG. 13) in a tomographic plane 40 by acquiring a phase distribution in a tomographic plane 40 (see FIG. 5) based on the plurality of X-ray images 10 of the subject T captured at a plurality of relative positions between the imaging system CS and the subject T in a predetermined direction and the acquired tomographic position.

<Imaging X-Ray Image at a Plurality of Relative Positions>

FIG. 4 is a schematic diagram of the plurality of X-ray images 10 captured while linearly moving the subject T in the X-direction by the moving mechanism 8. In the first embodiment, the moving mechanism 8 is configured to move the imaging system CS and the subject T to a plurality of relative positions by repeating the moving and the stopping of the relative movement of the imaging system CS and the subject T when imaging the subject T. The image processing unit 6 is configured to generate a phase-contrast image 16 based on the respective X-ray images 10 captured at the plurality of relative positions.

Specifically, FIG. 4 shows an example in which imaging is performed while moving the subject T from one side (right side) of the imaging region to the other side (left side) thereof to six relative positions, i.e., the first imaging position to the sixth imaging position. In the first imaging position, a part of the subject T in the X-direction is arranged outside the detection surface range of the detector 5, so the part of the subject T is not reflected in the X-ray image 10. In FIG. 4, focusing on the point Q fixed to the subject T, the position coordinate of the point Q in each X-ray image 10 changes according to the change in the relative position.

The control unit 7 moves the subject T to each imaging position when a command value corresponding to a movement amount to position the subject T to each relative position is inputted to the moving mechanism 8. The command value to the moving mechanism 8 is, for example, the number of pulses to be inputted to the moving mechanism 8 (drive source 8b). The control unit 7 moves the subject T by a distance of at least one period D4 or more of the Moire fringe 30 by the moving mechanism 8. In other words, the movement amount from the first imaging position, which is the initial imaging position, to the sixth imaging position, which is the last imaging position, is equal to or greater than one period D4 or more of the Moire fringe 30. With this, based on the respective X-ray images 10, for each pixel constituting the image of the subject T, the pixel value change (i.e., phase change) of one period or more of the Moire fringe 30 can be acquired.

Figure 5:
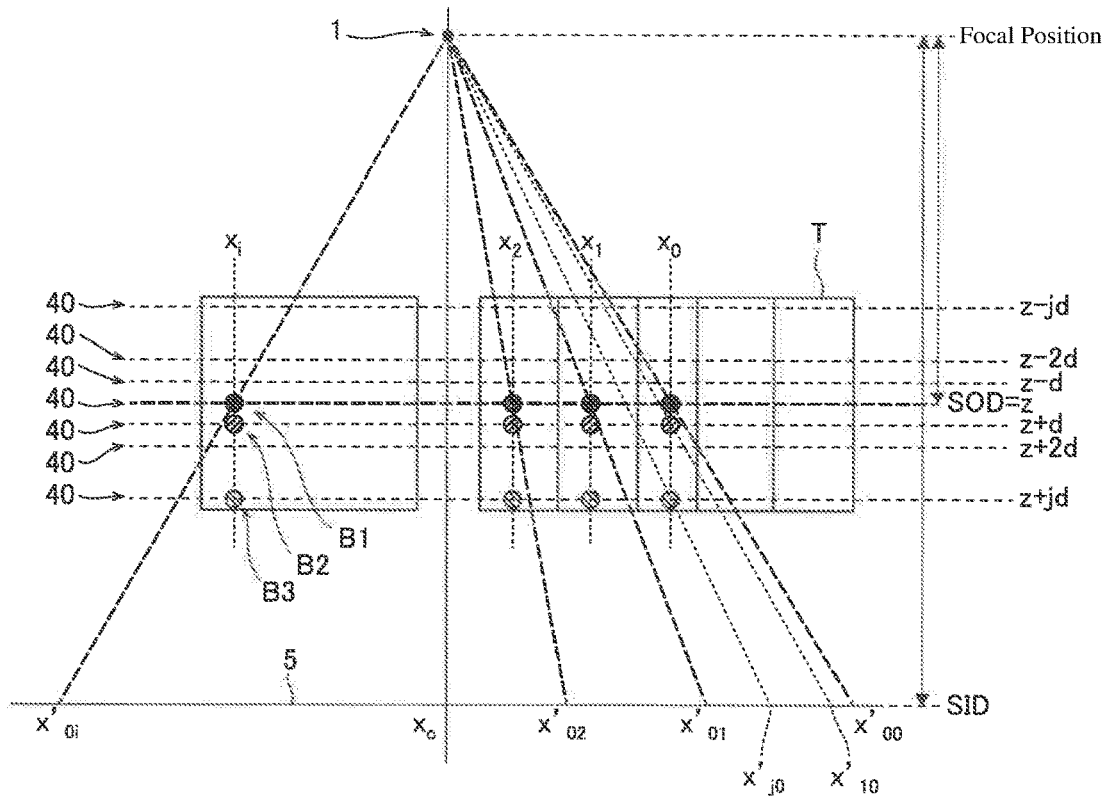
FIG. 5 is a schematic diagram for explaining a relationship between a relative position between an imaging system and a subject and a position coordinate in an X-ray image to be captured.

FIG. 5 is a diagram illustrating the relationship between the subject T and the position coordinate of the X-ray image 10 when capturing the X-ray image at a plurality of relative positions as described above. In FIG. 5, the vertical axis shows the position in the optical axis direction (Z-direction), and the horizontal axis shows the position in a predetermined direction (X-direction) to perform the relative movements. In the optical axis direction, the focal position of the X-ray source 1 is considered as the origin. As the position in the optical axis direction, the position away from the focal point by a distance SOD (source object distance) from the focal point to the center position of the subject T is referred to as a reference position (hereinafter, referred to as "SOD"). The position away from the focal point by a distance from the focal point to the detection surface of the detector 5 is defined as a detection surface position SID (source image distance).

In the first embodiment, the tomographic position of the tomographic plane 40 of the subject T is expressed as a deviation from the reference position SOD. In FIG. 5, as tomographic planes 40 of the subject T, "2j+1" pieces of tomographic planes 40 (including the tomographic plane of the reference position SOD) each shifted by a slice thickness d are set. The slice thickness "d" is a distance between the tomographic planes 40, and the tomographic planes 40 are arranged at even intervals shifted by the slice thickness "d"

in the optical axis direction. "j" is a tomographic position number, "+j" pieces of tomographic images 40 are set on the positive side (detector 5 side) with respect to the reference position SOD, and "−j" pieces of tomographic images 40 are set on the negative side (X-ray source 1 side) with respect to the reference position SOD. Assuming that the coordinate of the SOD in the optical axis direction is "z", the tomographic position of each tomographic plane 40 is expressed by (z−jd) to (z+jd).

The position information acquisition unit 7a is configured to acquire the deviation of the tomographic position relative to the reference position SOD in the optical axis direction. That is, the position information acquisition unit 7a acquires the slice thickness d and the tomographic position number (j) of the tomographic plane 40 as a tomographic position (z±jd) of the tomographic plane 40 to be imaged in the optical axis direction. Note that the position information acquisition unit 7a acquires the reference position SOD as known information.

Then, the image processing unit 6 is configured to acquire the phase distribution in the tomographic plane 40 based on the deviation (±jd) between the reference position SOD (=z) and the tomographic position relative to the reference position SOD in the optical axis direction and the relative position between the imaging system CS and the subject T in a predetermined direction (X-direction).

Figure 6:
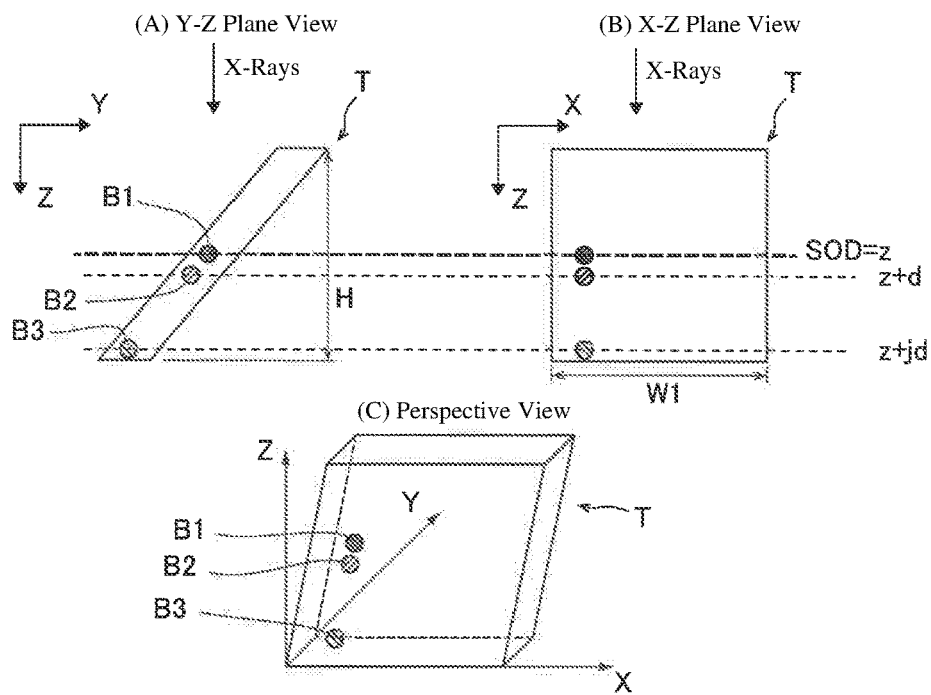
FIG. 6 shows a Y-Z plan view (A), an X-Z plan view (B), and a perspective view (C) of a subject for the explanation.

Here, for convenience of explanation, it is assumed the subject T has the shape shown in FIG. 6. The subject T has a thickness H in the optical axis direction (Z-direction) and a width W1 in the X-direction (predetermined orientation). Of the subject T, it is assumed that there are three points B1, B2, and B3 at the same position in the X-direction, and each of these points B1 to B3 is used as a reference of the X-direction position coordinate of the subject T in each tomographic plane 40. The point B1 is in the position of z (tomographic position number=0) in the optical axis direction. The point B2 is in the position of z+d (tomographic position number=1), and the point B3 is in the position of z+jd (tomographic position number=j).

Note that the subject T of FIG. 6 is inclined toward the Y-direction, and each of the points B1 to B3 is in a position shifted in the Y-direction. The reason that each of the points B1 to B3 is shifted in the Y-direction is set is for convenience so that each of the points B1 to B3 is reflected in positions shifted in the Y-direction in the X-ray image 10 corresponding to the X-Y perspective view of the subject T.

As shown in FIG. 5, the subject T is moved to the respective relative positions by the moving mechanism 8 and is imaged. The position of the subject T in the coordinate system on the moving mechanism 8 is represented by x ($x_0$ to $x_1$). "i" is the number used to identify the relative position, for example, the first imaging position to the sixth imaging position in FIG. 4 are identified as $x_1$ to $x_6$ when $x_0$ is an initial position.

The X-coordinate of the projected point of the point belonging to each tomographic plane 40 (0 to +j) to the detection surface (X-ray image 10) in each position coordinate $x_0$ to $x_i$ is set as x' ($x'_{00}$ to $x_{ji}$). Note that the same is applies to the tomographic plane 40 (0 to −j).

When the points B1 to B3 of the subject T are moved to the position $x_0$, the X-rays passing through the point B1 (tomographic position number=0) is reflected in the coordinate $x'_{00}$ of the detection surface (X-ray image 10). On the other hand, the X-rays passing through the point B2 (tomographic position number=1) is reflected in the coordinate of the $x'_{10}$ of the detection surface (X-ray image 10), and the X-rays passing through the point B3 (tomographic position number=j) is reflected in the coordinate of the $x'_{j0}$ of the detection surface (X-ray image 10). When the position coordinate $x_i$ of the subject T and the tomographic position (tomographic position number j) are determined, the position coordinate $x'_{ji}$ of the detection surface (X-ray image 10) is identified. For this reason, the relative position between the imaging system CS and the subject T is represented by $x_i$ in the coordinate system of the moving mechanism 8, and $x'_{ji}$ in the coordinate system of the X-ray image 10.

As shown in FIG. 5, when the thickness H of the subject T is large, the position coordinate x' where each of the points B1 to B3 at the same position in the X-direction is reflected is shifted on the X-ray image 10. Therefore, when a phase-contrast image 16 is generated from each X-ray image 10 simply based on the SOD, blurring occurs at the points B2 and B3, making it difficult to clearly image them. Therefore, in the first embodiment, the image processing unit 6 is configured to perform a coordinate transformation of the position coordinate in each X-ray image 10 to the coordinate system on the tomographic plane 40 based on the relative position ($x'_{ji}$) of each X-ray image 10 at the time of imaging and the acquired tomographic position (z+jd) and acquire the phase distribution in the tomographic plane 40 based on the pixel value of each X-ray image 10 after the coordinate transformation.

Figure 7:
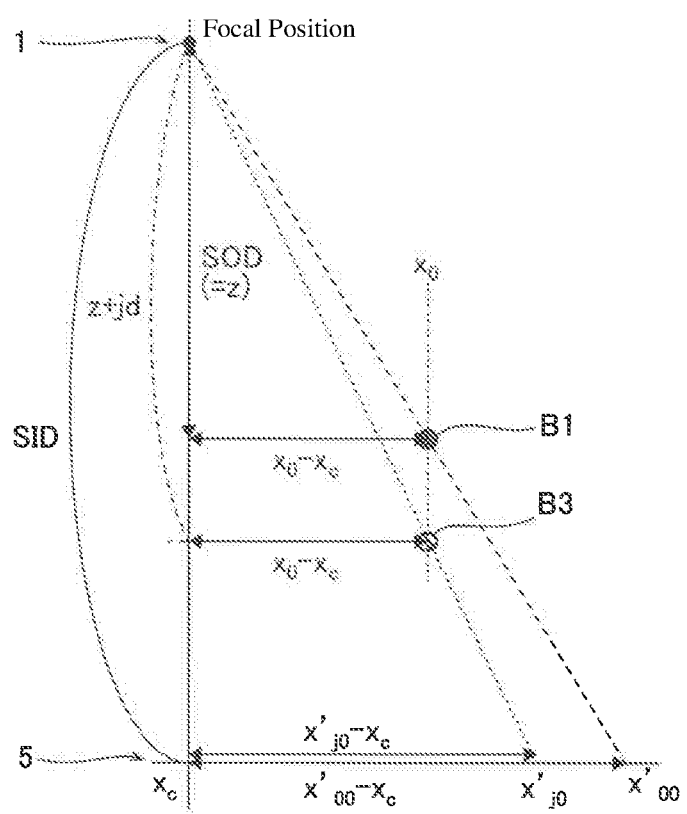
FIG. 7 is a diagram showing a geometrical relationship between an X-ray source, points on a tomographic plane in a subject, and a detector.

Specifically, in FIG. 5, the point B1 of the tomographic position number j=0 at the position $x_0$ of the subject T and the position coordinate $x'_{00}$ on the detection surface (X-ray image 10) are expressed by the following relational expression because of the similarity relation shown in FIG. 7. $x_c$ represents the X-coordinate of the optical axis (normal line passing through the focal point) on the detection surface (X-ray image 10).

$$x'_{00} - x_c = (x_0 - x_c)\frac{SID}{SOD} = (x_0 - x_c)\frac{SID}{z} \quad (1)$$

Here, at the position $x_0$ of the subject T, for the point (point B3) at the $j^{th}$ tomographic position z+jd from the reference position SOD, the X coordinate $x'_{j0}$ reflecting on the detection surface (X-ray image 10) is represented by the following relational expression because of the similarity relation shown in FIG. 7.

$$x'_{j0} - x_c = (x_0 - x_c)\frac{SID}{z+jd} = \frac{z}{z+jd}(x'_{00} - x_c) \quad (2)$$

As can be understood from Expression (2), it is possible to perform the transformation from the position coordinate $x'_{00}$ on the reference position SOD (=z) to the position coordinate $x'_{j0}$ on any tomographic plane 40. The position coordinate $x'_{00}$ and the position coordinate $x'_{j0}$ are represented by the relation independent of the SOD.

Therefore, when the subject T is moved to any $i^{th}$ position $x_i$ by the moving mechanism 8, the position coordinate $x'_{ji}$ of the point at any $j^{th}$ tomographic position is represented by the following Expression (3).

$$x'_{ji} - x_c = \frac{z}{z+jd}(x'_{0i} - x_c) \quad (3)$$

By arranging the above Expression (3), the following Expression (4) is acquired.

$$x'_{ji} = \frac{z}{z+jd}x'_{0i} + \left(1 - \frac{z}{z+jd}\right)x_c \quad (4)$$

From the above, the position coordinate of each X-ray image 10 in which the subject T is imaged at each relative position $x_i$ of the subject T in a predetermined (X-direction) moved by the moving mechanism 8 can be converted into a position coordinate of the tomographic image on the tomographic plane 40 at any tomographic position (z+jd) deviating from the reference position SOD.

Thus, the image processing unit 6 is configured to acquire the phase distribution in the tomographic plane 40 based on the deviation (jd) between the reference position SOD (=z) in the optical axis direction and the tomographic position relative to the reference position SOD and the relative position ($x'_{0i}$) between the imaging system CS and the subject T in the predetermined direction (X-direction).

Note that the relative position ($x'_{0i}$) of the subject T is acquired by the following Expression (5).

$$x'_{0i} = x_{start} p1 \times np \quad (5)$$

Here, $X_{start}$ is the initial position of the subject T at the imaging initiation time. Also, p1 is the transformation coefficient [pixel/pulse] of the actual movement amount of the subject T in the X-ray image 10 for the command value (number of pulses) inputted to the moving mechanism 8. "np" is a command value (number of pulses) inputted to the moving mechanism 8 when moving the subject T to the respective relative positions $x_0$ to $x_i$.

The image processing unit 6 acquires each relative position ($x'_{0i}$) of the subject T by the above Expression (5) for each of the acquired X-ray images 10 and substitutes it into the above Expression (4) to perform a coordinate transformation so as to become a tomographic image of the tomographic plane 40 specified by the tomographic position number j.

(Generation of Position Calibration Data)

In the above Expression (5), the transformation coefficient p1 [pixel/pulse] is a part of the design specification of the moving mechanism 8 and can be acquired in advance as known information. On the other hand, in the first embodiment, the image processing unit 6 is configured to generate position calibration data 45 (see FIG. 1) that associates the movement amount of the moving mechanism 8 with the change amount of the relative position ($x'_{0i}$) in the X-ray image 10 and acquire the phase distribution in the tomographic plane 40 using the position calibration data 45 acquired at the reference position SOD.

Figure 8:
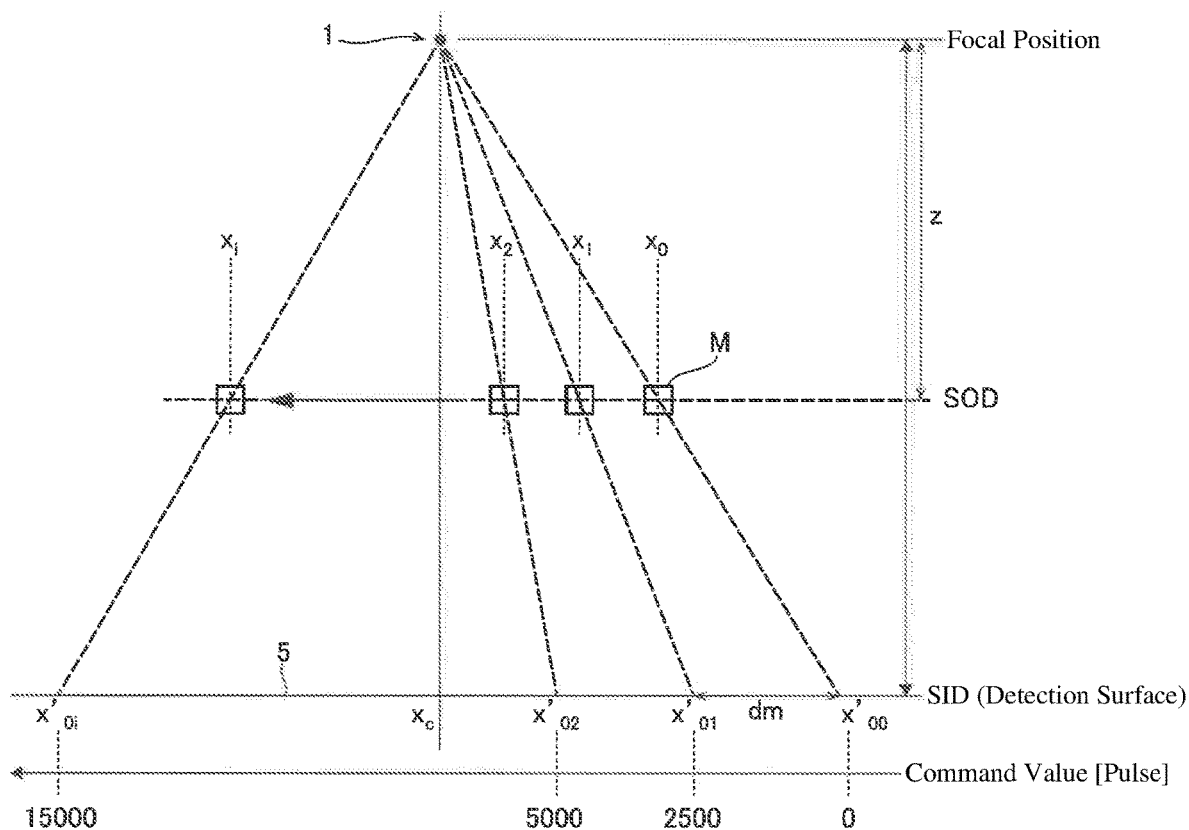
FIG. 8 is a schematic diagram showing a relative position when imaging a plurality of position calibration images.

Specifically, as shown in FIG. 8, the image processing unit 6 generates position calibration data 45 including the conversion coefficient p1 based on a plurality of position calibration images 13 (see FIG. 9) in which a marker M arranged at the reference position SOD in the optical axis direction is imaged at a plurality of relative positions in a predetermined direction.

The marker M is not particularly limited as long as it can distinguish a predetermined X-direction (X-direction) position coordinate on the X-ray image but is preferably an object low in X-ray transmittance, small in thickness and small in width in the X-direction. The marker M may be, for example, a linear wire member or a rod member, or a marker member linearly provided on a plastic plate or the like.

The position calibration data 45 is generated based on the command value to be inputted to the moving mechanism 8 and the actual position change dm (see FIG. 8) of the marker M in the position calibration image 13. The position calibration data 45 is generated as an approximate expression shown in the above-described Expression (5), which represents the relation between the command value and the position change dm of the marker M.

Figure 9:
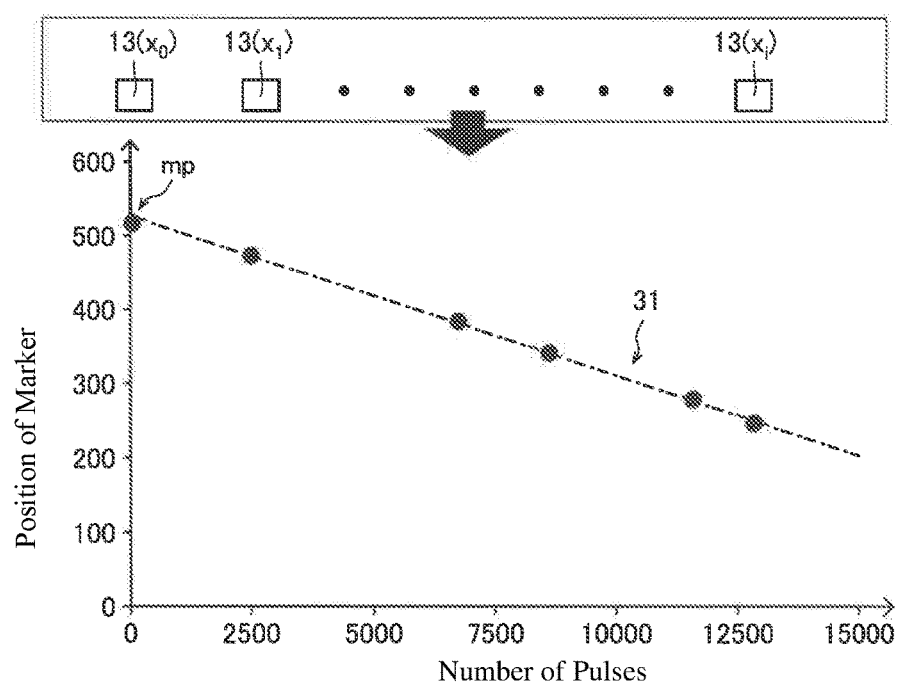
FIG. 9 is a schematic diagram for explaining a method of acquiring position calibration data.

FIG. 9 is a graph in which the vertical axis represents the position [pixel] of the marker M in each position calibration image 13 and the horizontal axis represents the command value [pulse] when moving the marker M. The plot mp in the graph 31 is a point obtained by plotting the inputted command value and the value of the relative position ($x'_{0i}$) of the actually moved marker M. The image processing unit 6 acquires the transformation coefficient p1 in the above-described Expression (5) by linearly fitting the values of the respective plots mp acquired from the plurality of position calibration images 13.

In the first embodiment, the moving mechanism 8 is configured to relatively move the imaging system CS and the subject T to the same relative position as each relative position between the imaging system CS and the marker M at the time of generating the position calibration data 45 when imaging the subject T. That is, when generating the position calibration data 45, the processing unit 6 moves the marker M to the relative positions $x_0$ to $x_i$ by the moving mechanism 8 to acquire the respective position calibration images 13. With this, the position calibration data 45 is generated from the actual measurement values of the position coordinates ($X'_{00}$ to $X'_{0i}$) on the cross-section of the reference position SOD. When imaging the subject T, the image processing unit 6 moves the subject T to the same relative position $x_0$ to $x_i$ by the moving mechanism 8 to acquire the X-ray image 10. With this, the error of the position coordinate ($x'_{00}$ to $x'_{0i}$) on the cross-section of the reference position SOD at the time of imaging the subject T is reduced as much as possible using the position calibration data 45 (the above-described Expression (5)) including the transformation coefficient p1.

(Phase Information of Moire Fringe)

Next, the configuration for acquiring the phase distribution in the tomographic plane 40 will be described. Apart from the imaging of the subject T, the X-ray imaging device 100 acquires a Moire fringe image 11 in each Step as shown in FIG. 10 by translating the first grating 2 stepwise (in a stepwise manner) by the grating moving mechanism 9. Each Moire fringe image 11 is acquired by capturing a Moire fringe 30 moved on the detection surface of the detector 5 by translating the first grating 2 and is an image reflecting the striped pattern due to the light and darkness of the pixel value of the Moire fringe 30. The translational movement of the grating is made by performing the step movement of a (1/M) period by M times, the (1/M) being obtained by dividing one period of the Moire fringe 30 by M, to thereby move the grating by the distance of a total one period. The image processing unit 6 is configured to acquire the phase information 12 of the Moire fringe 30 based on each Moire fringe image 11. FIG. 10 shows an example of M=4.

Specifically, the Moire fringe image 11 of the first to fourth Steps of FIG. 10 is defined as $I_k$ (x, y), and S (x, y) is defined as shown in the following Expression (6).

$$S(x, y) = \sum_{k=1}^{M} I_k(x, y)\exp\left(-\frac{2i\pi k}{M}\right) \quad (6)$$

Where "k" is the number of each step. x and y are the pixel position (position coordinate) on the detection surface of the detector 5.

Using the above-described Expression (6), the phase information 12 of the Moire fringe 30 is represented by the following Expression (7).

$$\varphi(x,y)=arg[S(x,y)] \quad (7)$$

Here, φ(x, y) is phase information 12 of the Moire fringe 30. It should be noted that $I_k$ (x, y) may be a function of k, a sine curve (sine-wave) may be used for fitting, and the phase information of the sine curve may be the phase information 12 of the Moire fringe 30.

The phase information 12 of the Moire fringe 30 shown in FIG. 10 shows that each pixel value represents the phase value at its position coordinate. In the phase information 12, the variation of a 2π (1 period) range of the phase value of the Moire fringe 30 appears as a stripe pattern. By the phase information 12, the phase value in each position coordinate of the X-ray image 10 is acquired.

Using the above-described Expression (4) and Expression (5), the image processing unit 6 performs a coordinate transformation to the tomographic image ($x'_{j0}$ to $x'_{ji}$) of any cross-section position (z±jd) of the X-ray image 10 ($x'_{00}$ to $x'_{0i}$) in each relative position at the reference position SOD and also performs a coordinate transformation for each relative position for the phase information 12 of the Moire fringe 30. Consequently, for example, in the tomographic plane 40 including the point B3 in FIG. 5, for each of the X-ray image 10 and the phase information 12, a coordinate transformation to the stationary coordinate system in which the position coordinates where the point B3 (subject T) is reflected coincide is performed.

Figure 11:
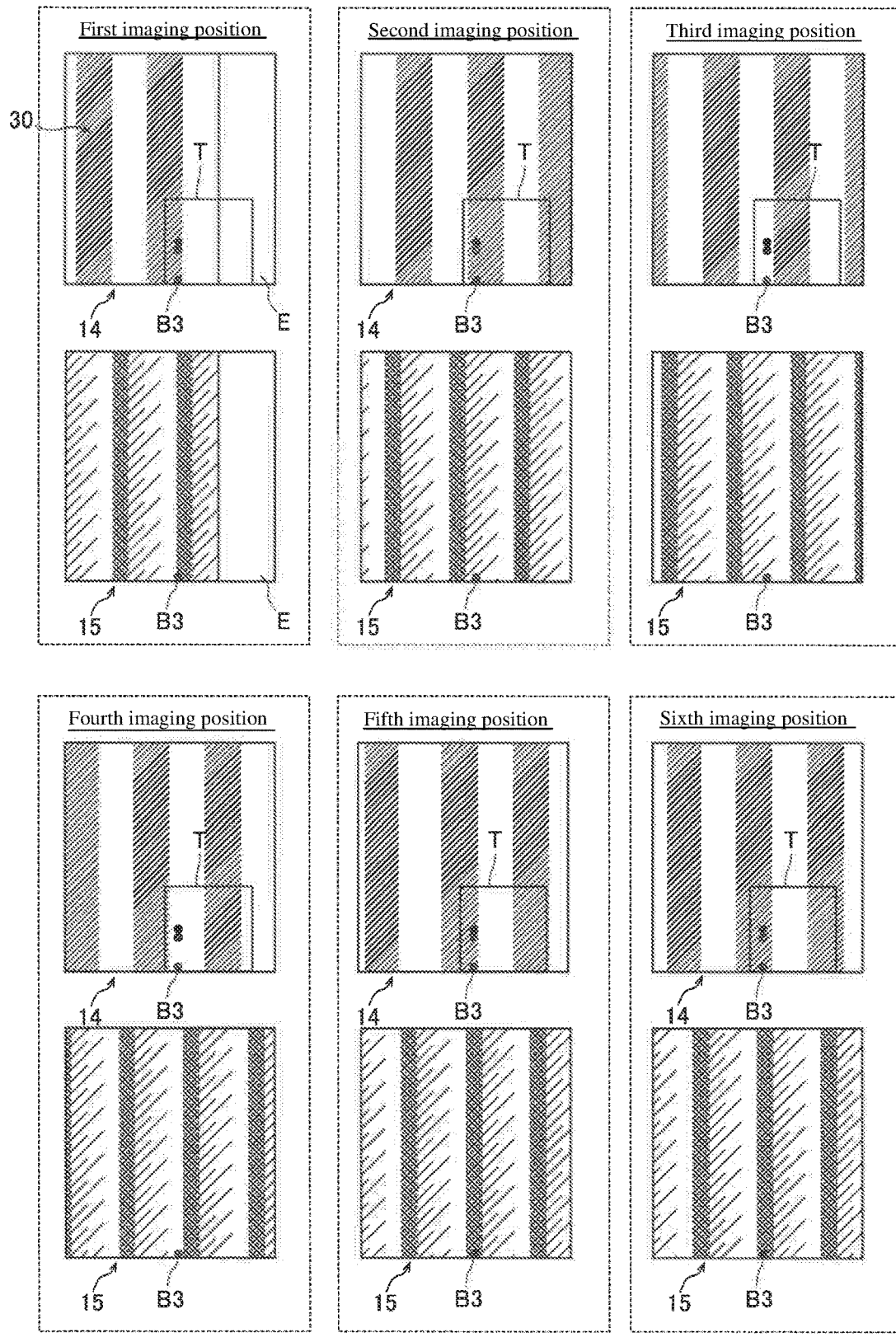
FIG. 11 is a schematic diagram showing a plurality of X-ray images and phase information after a coordinate transformation when the coordinate transformation is performed to a stationary coordinate system in a subject on a tomographic plane.

As shown in FIG. 11, in each X-ray image 14 after the coordinate transformation, the position of the subject T (point B3) is fixed and the Moire fringe 30 moves relative to the subject T. Further, in the phase information 15 after the coordinate transformation, the distribution of the phase value is moved according to the movement of the Moire fringe 30 in each X-ray image 10 after the coordinate transformation. That is, the position of the pixel in each imaging position after the coordinate transformation and the position of the phase value of the Moire fringe 30 in the phase information 15 correspond to each other in a one-to-one relation with reference to the subject T.

Figure 12:
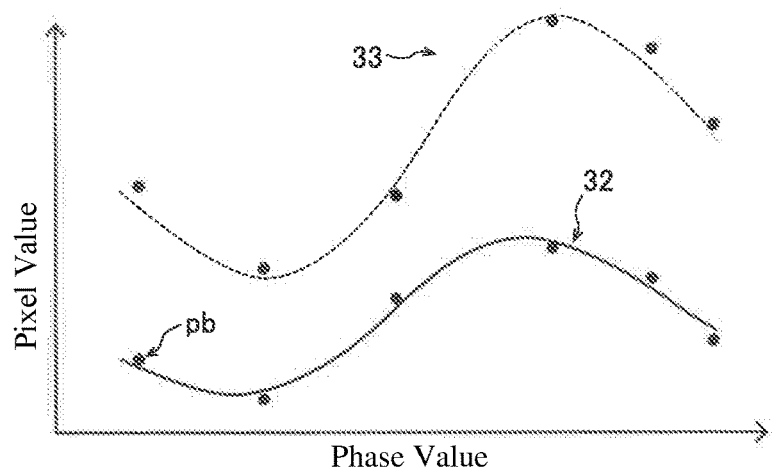
FIG. 12 is a schematic diagram of an intensity signal curve between a phase value and a pixel value of each pixel of an X-ray image.

As shown in FIG. 12, the image processing unit 6 acquires the intensity signal curve 32 of the pixel value in which each pixel value in the plurality of X-ray images 14 and the phase value of each pixel are associated in a one-to-one relation using each X-ray image 14 after the coordinate transformation and the phase information 15 after the coordinate transformation. In the intensity signal curve 32, the horizontal axis represents the phase value and the vertical axis represents the pixel value. FIG. 12 is an example of the intensity signal curve 32 acquired by, for example, acquiring a plot pb based on the pixel value at the point B3 of the plurality of X-ray images 14 and the phase value at the point B3 of the plurality of phase information 15 and fitting by a sine wave. For the blank region E shown in FIG. 11, since there is no phase information 12 of the Moire fringe 30, no sampling is performed in FIG. 12. The image processing unit 6 acquires the intensity signal curve 32 for each pixel of the X-ray image 14 after the coordinate transformation as the phase distribution in the tomographic plane 40.

Figure 13:
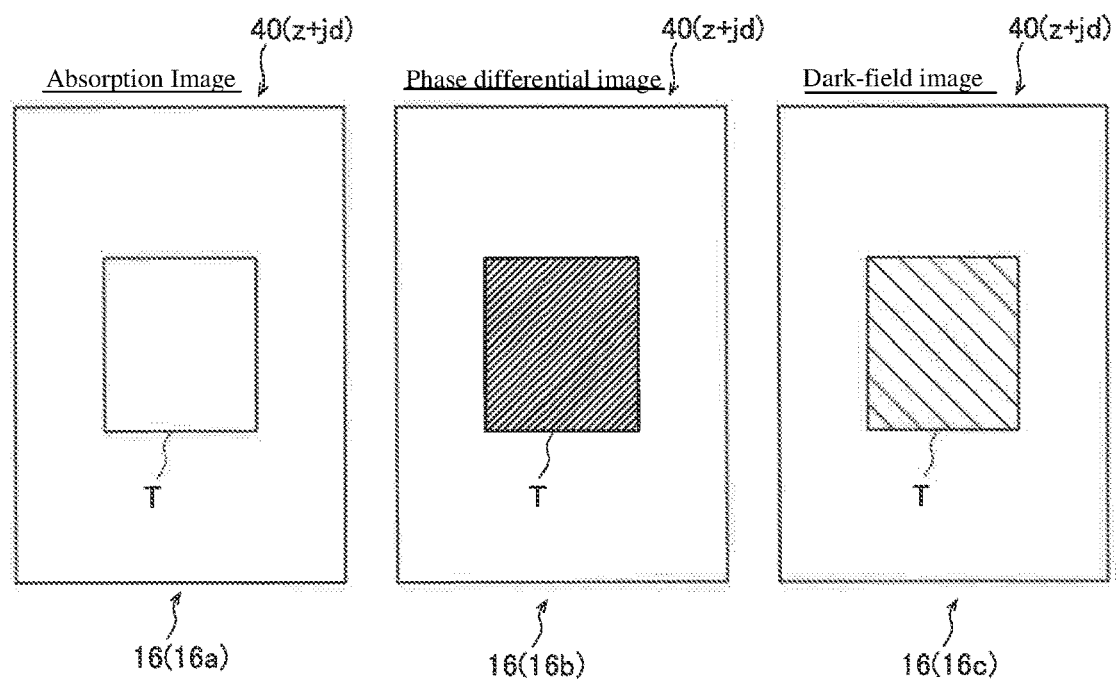
FIG. 13 is a schematic diagram of a phase-contrast image generated by an image processing unit according to the first embodiment.

The image processing unit 6 is configured to generate a phase-contrast image 16 (tomographic image) in the tomographic plane 40 based on the acquired intensity signal curve 32. Specifically, as shown in FIG. 13, the image processing unit 6 generates an absorption image 16*a*, a phase differential image 16*b*, and a dark-field image 16*c*.

The image processing unit 6 generates an average value image (not shown) from the constant value (average value) of the intensity signal curve 32 of the X-ray image 14 after the coordinate transformation. The image processing unit 6 generates a phase image (not shown) from the phase value of the intensity signal curve 32. The image processing unit 6 generates a visibility image (not shown) from the amplitude/constant value of the intensity signal curve 32. It may be enough to merely generate these of the average value image, the phase image, and the visibility image as phase-contrast images 16.

At the timing before imaging or after imaging the subject T, the image processing unit 6 acquires an air image (not shown) captured without arranging the subject T acquires the intensity signal curve 33 (see FIG. 12) for each pixel of the air image after the coordinate transformation, and generates an average value image, a phase image, and a visibility image without the subject in the same manner as in the X-ray image 14 acquired by imaging the subject T. The image processing unit 6 generates an absorption image 16*a* based on the ratio of the average value image with the subject and that without the subject. The image processing unit 6 generates a phase differential image 16*b* based on the difference between the phase image with the subject and that without the subject. The image processing unit 6 generates a dark-field image 16*c* based on the ratio of the visibility image with the subject and that without the subject. Since the method for generating each image is known, the detailed description thereof will be omitted. The image processing unit 6 performs the tasks from the above-described coordinate transformation to the extraction of the phase-contrast image (i.e., the coordinate transformation of the X-ray image 14, the acquisition of the intensity signal curve 32 for each pixel of the X-ray image 14 after the coordinate transformation, the generation of the phase-contrast image 16 (tomographic image) in the tomographic plane 40 based on the acquired intensity signal curve 32) for each tomographic plane 40.

Figure 14:
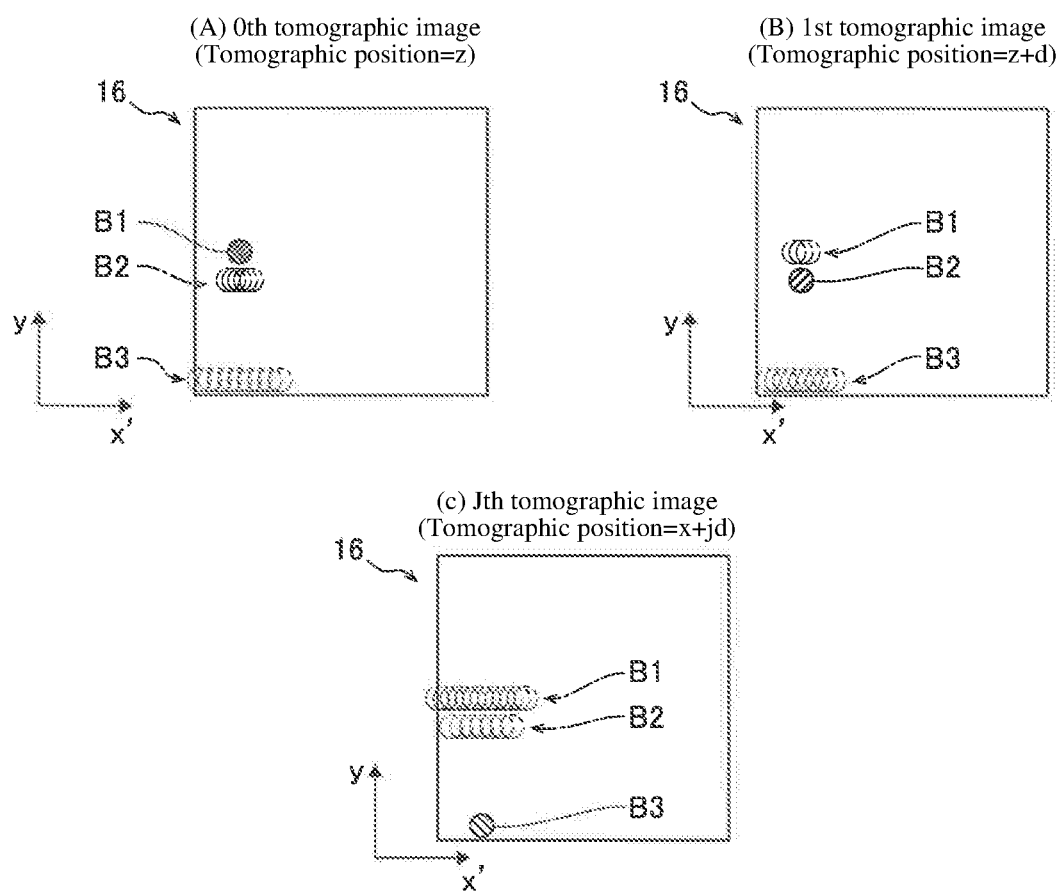
FIG. 14 shows schematic diagrams (A) to (C) for explaining how a subject is reflected in a tomographic image at each tomographic position.

The generated absorption image 16*a*, phase differential image 16*b*, and dark-field image 16*c* are tomographic images at the tomographic position (z+jd) acquired by the position information acquisition unit 7*a*. FIG. 14 is a conceptual diagram of the tomographic image (phase-contrast tomographic image) of the phase-contrast image 16. As shown in FIG. 14(A), for example, when the reference position SOD (=z) is taken as the tomographic position, the X-ray image 10 and the phase information 12 are converted into the stationary coordinate system of the subject T with reference to the point B1 on the tomographic plane 40 of the tomographic position=z, thereby generating a tomographic image (absorption image 16*a*, phase differential image 16*b*, dark-field image 16*c*) focused on the tomographic plane 40 at the tomographic position=z. At this time, in the image at the point B2 and that at the point B3 in different tomographic planes 40, blurring occurs.

As shown in FIG. 14(B), when the tomographic position (z+d) of the tomographic plane 40 with the point B2 is taken, it is converted into the stationary coordinate system of the subject T with reference to the point B2 on the tomographic plane 40 at the tomographic position=z+d, thereby generating a tomographic image focused on the tomographic plane 40 at the tomographic position=z+d. At this time, in the image at the point B1 and that at the point B3 in different tomographic planes 40, blurring occurs.

As shown in FIG. 14(C), when the tomographic position (z+jd) of the tomographic plane 40 with the point B3 is taken, it is converted into the stationary coordinate system of subject T with reference to the point B3 on the tomographic plane 40 at the tomographic position=z+j d, thereby generating a tomographic image focused on the tomographic plane 40 at the tomographic position=z+jd. At this time, in the image at the point B1 and that at the point B2 in different tomographic planes 40, blurring occurs.

As described above, in the first embodiment, a phase-contrast tomographic image in which blurring is suppressed (image is focused) at any tomographic plane 40 specified by the user can be provided.

Figure 15:
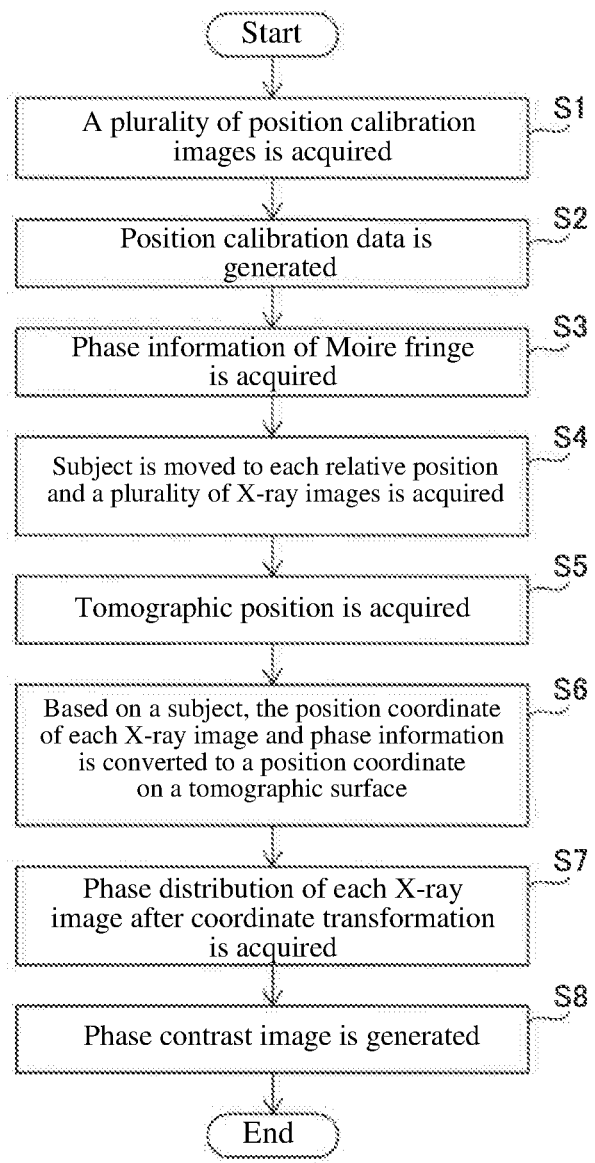
FIG. 15 is a flowchart for explaining generation processing of a phase-contrast image by the X-ray imaging device according to the first embodiment.

Next, referring to FIG. 15, the flow of processing for generating a phase-contrast image 16 by the X-ray imaging device 100 according to the first embodiment will be described.

In Step S1, the control unit 7 performs imaging of the marker M at each relative position while moving the marker M to the relative positions $x_0$ to $x_i$ by the moving mechanism 8. The control unit 7 acquires a command value of the subject T at each relative position. The image processing unit 6 generates a plurality of position calibration images 13 at each relative position.

In Step S2, the image processing unit 6 acquires the movement amount dm of the subject T in the position calibration image 13 of each relative position under the control of the control unit 7 and acquires the approximate expression (position calibration data 45) based on the movement amount dm of the marker M and the command value.

In Step S3, the image processing unit 6 acquires the phase information 12 of the Moire fringe 30. In Step S4, the image processing unit 6 acquires a plurality of X-ray images 10 at a plurality of relative positions in the X-direction by the moving mechanism 8. The moving mechanism 8 moves the subject T to the relative positions $x_0$ to $x_i$. At this time, an air image (not shown) with no subject is also acquired.

In Step S5, the position information acquisition unit 7a acquires the tomographic position. The position information acquisition unit 7a acquires each set value of the SOD (=z), the slice thickness d, and the tomographic position number j, which are set by, for example, the user. The acquisition processing of the tomographic position (z+jd) may be performed at any time prior to Step S6.

In Step S6, the image processing unit 6 performs the position transformation of the position coordinate of each X-ray image 10 and each phase information 12 acquired at each relative position with reference to a point on the tomographic plane 40 specified by the acquired tomographic position (z+jd) in the subject T. With this, the image processing unit 6 acquires each X-ray image 14 and each phase information 15 after the coordinate transformation, which is transformed to a stationary coordinate system with reference to the subject T on the tomographic plane 40.

In Step S7, the image processing unit 6 acquires the phase distribution in the tomographic plane 40 based on each X-ray image 14 and each phase information 15 after the coordinate transformation. That is, the image processing unit 6 generates the intensity signal curve 32 of each pixel (each position coordinate) in a stationary coordinate system with reference to the subject T on the tomographic plane 40.

In Step S8, the image processing unit 6 generates the phase-contrast image 16 based on the generated intensity signal curve 32. The image processing unit 6 generates the absorption image 16a, the phase differential image 16b, and the dark-field image 16c. This completes the generation processing of the phase-contrast image.

Note that either the acquisition processing of the position calibration data 45 in Step S1 and Step S2 or the acquisition processing of the phase information 12 of the Moire fringe 30 in Step S3 may be performed first. The acquisition processing of the position calibration data 45 may be performed at any timing as long as it is prior to performing the coordinate transformations of the plurality of X-ray images 10. Further, the processing of acquiring the phase information 12 of the Moire fringe 30 may be performed at any timing as long as it is prior to the coordinate transformation of the phase information 12.

Effects of First Embodiment

In this first embodiment, the following effects can be obtained.

In the first embodiment, as described above, it is provided with the position information acquisition unit 7a for acquiring the tomographic position (z+jd) of the tomographic plane 40 to be imaged in the optical axis direction and the image processing unit 6 for generating the phase-contrast image 16 in the tomographic plane 40 by acquiring the phase distribution in the tomographic plane 40 based on the plurality of X-ray images 10 in which the subject T was imaged at a plurality of relative positions between the imaging system CS and the subject T in the predetermined direction and the acquired tomographic position (z+jd). With this, it is possible to acquire the position (z+jd) of the tomographic plane 40 in the optical axis direction in which the internal structure to be imaged is present among the subject T can be acquired by the position information acquisition unit 7a. Then, the position of the point on the tomographic plane 40 in each X-ray image 10 can be identified by the information of the tomographic position (z+jd) and the relative position ($x'_{0i}$) when the X-ray image 10 is captured. Thus, by the image processing unit 6, the phase distribution in a particular tomographic plane 40 indicated by the tomographic position (z+jd) can be acquired based on the information of the acquired tomographic position (z+jd) and the respective X-ray images 10 at a plurality of relative positions. Consequently, from the phase distribution in the tomographic plane 40 at the tomographic position (z+jd) acquired by the position information acquisition unit 7a, the phase-contrast image 16 (phase-contrast tomographic image) in which the blurring of the image is suppressed for the internal structure included in the tomographic plane 40 is acquired. With this, even if the subject T has a large thickness, it is possible to suppress the deterioration of the visibility of the internal structure.

Note that when the tomographic position (tomographic position number j) to be acquired by the position information acquisition unit 7a is changed, the internal structure included in the tomographic plane 40 indicated by the changed tomographic position can be visually recognized by the phase-contrast image 16 (tomographic image) focused on the internal structure. Therefore, in the first embodiment, depending on the tomographic position at which the user wants to image, a phase-contrast image 16 (tomographic image) high in the visibility in any tomographic plane 40 can be acquired. Since the decrease in visibility due to blurring of an image gives a large impact as the internal structure to be imaged becomes finer, the above-described configuration is particularly useful when a detailed check of a fine structure or an internal structure is desired.

In the first embodiment, as described above, the image processing unit 6 is configured to perform the coordinate transformation of the position coordinate in each X-ray image 10 to the coordinate system on the tomographic plane 40 based on the relative position ($x'_{0i}$) at the time of imaging each X-ray image 10 and the acquired tomographic position (z+jd), and acquire the phase distribution in the tomographic plane 40 based on the pixel value of each X-ray image 14 after the coordinate transformation. As shown in FIG. 7, the geometric positional relation between the X-ray source 1, the subject T, and the detector 5 (i.e., the imaging system in the X-ray image 10) in each individual X-ray image 10 is determined from the relative position between the imaging system CS and the subject T and the tomographic position (z+jd). Therefore, by performing the coordinate transformation of the position coordinate of each X-ray image 10 so that the same position of the subject T on the tomographic plane 40 coincides with each other on X-ray image 10 utilizing the geometric relation, it is possible to easily acquire the phase distribution in the tomographic plane 40.

In the first embodiment, as described above, the position information acquisition unit 7a is configured to acquire the deviation (jd) of the tomographic position with respect to the reference position SOD in the optical axis direction, and the image processing unit 6 is configured to acquire the phase distribution in the tomographic plane 40 based on the deviation (jd) of the tomographic position between the reference position SOD (=z) in the optical axis direction and the tomographic position relative to the reference position SOD and the relative position between the imaging system CS and the subject T in the predetermined direction. With this, at the time of the imaging, by arranging the predetermined position such as the center of the subject T at the preset reference position SOD, the tomographic position of the subject T in the optical axis direction can be handled as a distance (deviation jd) from the reference position SOD. Consequently, the desired tomographic image can be easily acquired by easily specifying the tomographic position (z+jd) to be imaged in the subject T.

In the first embodiment, as described above, the image processing unit 6 is configured to generate the position calibration data 45 associating the movement amount of the moving mechanism 8 with the change amount of the relative position in the X-ray image 10 based on the plurality of position calibration images 13 acquired by imaging the marker M arranged at the reference position SOD in the optical axis direction at the plurality of relative positions in the predetermined direction, and acquire the phase distribution in the tomographic plane 40 using the position calibration data 45 acquired at the reference position SOD. This enables accurate acquisition of the actual position change on X-ray image 10 of the point (marker M) on the tomographic plane 40 passing through the reference position SOD. Since the position of the point on the tomographic plane 40 passing through the reference position SOD can be accurately grasped, the position coordinate on any tomographic plane 40 can be accurately grasped without generating the position calibration data 45 at each tomographic position (z+jd). Consequently, the phase distribution at any tomographic plane 40 acquired by the position information acquisition unit 7a can be acquired with high accuracy by simply generating the position calibration data 45 of the reference position SOD.

Further, in the first embodiment, as described above, when imaging the subject T, the moving mechanism 8 is configured so as to relatively move the imaging system CS and the subject T to the same relative position as each relative position ($x_i$) between the imaging system CS and the marker M at the time of generating the position calibration data 45. With this, since the phase-contrast tomographic image can be generated based on the X-ray image 10 captured at the same relative position as when generating the position calibration data 45, the relative position between the imaging system CS and the subject T in each X-ray image 10 can be more accurately identified by eliminating the error factor of the position calibration data 45 as much as possible.

Further, in the first embodiment, as described above, the moving mechanism 8 is configured so as to move the subject T to a plurality of relative positions ($x_i$) by repeatedly performing the relative movement of the imaging system CS and the subject T and the stopping thereof when imaging the subject T. With this, since it is possible to capture each X-ray image 10 in a stationary state, it is possible to capture the X-ray image 10 by suppressing the deviation of the relative position and blurring of the image as much as possible.

Further, in the first embodiment, as described above, the moving mechanism 8 is configured to move the subject T in a predetermined direction with respect to the imaging system CS. With this, unlike when moving the entire imaging system CS, it is sufficient to move only the subject T, it is possible to simplify and miniaturize the moving mechanism 8 and it is possible to easily secure the position accuracy during the movement.

Further, in the first embodiment, as described above, as a plurality of gratings, a third grating 4 arranged between the X-ray source 1 and the first grating 2 is provided. With this, it is possible to enhance the coherence of X-rays emitted from the X-ray source 1 by the third grating 4. Consequently, since it is possible to form the self-image of the first grating 2 even if the focal diameter of the X-ray source 1 is large, it is possible to improve the flexibility in selecting the X-ray source 1.

Second Embodiment

Figure 16:
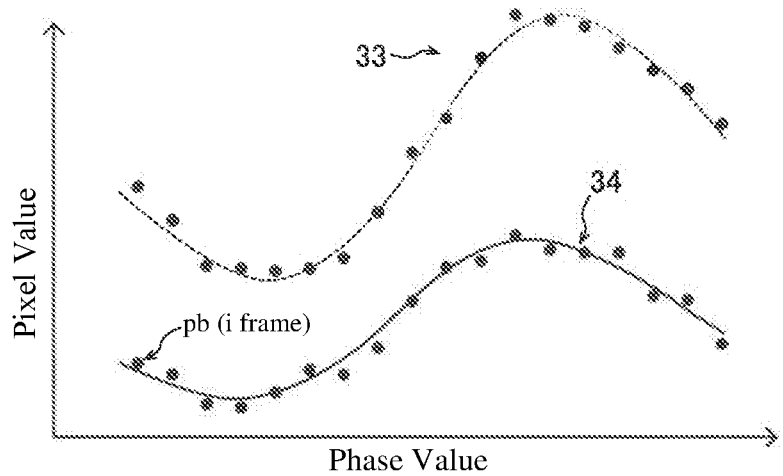
FIG. 16 is a schematic diagram of an intensity signal curve between a phase value and a pixel value at each pixel of an X-ray image according to a second embodiment.

Next, referring to FIG. 1 and FIG. 16, an X-ray imaging device 200 (see FIG. 1) according to a second embodiment will be described. Unlike the above-described first embodiment in which the subject T is moved to a plurality of relative positions (xi) by repeating the relative movement and stopping, in the second embodiment, the moving mechanism 8 continuously moves the subject T when imaging the subject T. Note that the same configuration as that of the above-described first embodiment is denoted by the same reference symbol, and the description thereof will be omitted.

(Configuration of X-Ray Imaging Device)

In the second embodiment, the moving mechanism 8 (see FIG. 1) is configured to continuously and relatively move the imaging system CS and the subject T when imaging the subject T. Further, the image processing unit 6 is configured to generate the phase-contrast image 16 based on the respective X-ray images 10 acquired continuously. That is, in the second embodiment, each X-ray image 10 is acquired as a moving image continuously captured at predetermined frame rates (time intervals).

In the second embodiment, in order to acquire the X-ray image 10 as a moving image, the image processing unit 6 acquires the following Expression (8) as the position calibration data 45.

$$x'_{0i} = x_{start} + p1 \times vp \times (1/fps) \times i \qquad (8)$$

Where vp is a rate (pulse/s) when the moving mechanism 8 moves the subject T. Further, fps is a frame rate (frame/s) when capturing the moving image. Further, "i" is the frame number in the moving image.

In the second embodiment, each X-ray image 10 is a frame image of a moving image. $X_{start}$ is the initial position of the subject T in the first frame. The position coordinate $x_i$ of the subject T in the coordinate system of the moving mechanism 8 represents the position of the subject T in the i-frame. ($x'_{0i}$) indicates the position coordinate of the subject T in the i-frame image of j=0 tomography.

The image processing unit 6 performs the coordinate transformation to a tomographic image at any tomographic position (z±jd) by substituting the position coordinate ($x'_{00}$ to $x'_{0i}$) acquired by using the position calibration data 45 to Expression (4). The image processing unit 6, in the same manner as in the first embodiment, acquires the intensity signal curve 34 shown in FIG. 16 based on the pixel of each X-ray image 14 after the coordinate transformation and the phase information 15 after the coordinate transformation. In the intensity signal curve 34, in the same manner as in the intensity signal curve 32 in the first embodiment, the horizontal axis represents the phase value, and the vertical axis represents the pixel value. Also in the second embodiment, in the same manner as in the first embodiment, the image processing unit 6 generates the phase-contrast image 16 based on the intensity signal curve 34.

The rest of the configuration of the second embodiment is the same as that of the first embodiment.

Effects of Second Embodiment

In this second embodiment, the following effects can be obtained.

In the second embodiment, as described above, when imaging the subject T, the moving mechanism 8 is configured to continuously and relatively move the imaging system CS and the subject T, and the image processing unit 6 is configured to generate the phase-contrast images 16 based on the continuously acquired X-ray images 10. With this, even when imaging the X-ray image 10 at a plurality of relative positions, it is possible to complete the imaging in a short time, so that it is possible to quickly acquire the phase-contrast image 16 of the desired tomographic position (z+jd). Further, by completing the imaging in a short time, it is possible to suppress the effects such as the deviation of the relative position due to thermal variations during imaging each X-ray image 10.

The other effects of the second embodiment are the same as those of the above-described first embodiment.

Third Embodiment

Next, referring to FIG. 1, FIG. 5, FIG. 17, and FIG. 18, an X-ray imaging device 300 (see FIG. 1) according to a third embodiment will be described. In the third embodiment, unlike the first and second embodiments in which a phase-contrast image 16 in the tomographic plane 40 at any tomographic position is generated, an example is shown in which three-dimensional data 50 of the subject T is generated based on the respective phase-contrast images 16 in the plurality of tomographic planes 40. Note that the same configurations as those of the first and second embodiments are denoted by the same reference symbols, and the descriptions thereof will be omitted.

(Configuration of X-Ray Imaging Device)

In the third embodiment, the position information acquisition unit 7a (see FIG. 1) is configured to acquire the tomographic position (z+jd) (see FIG. 5) of the plurality of tomographic planes 40 shifted in the optical axis direction. The number of tomographic planes 40 and the position of the tomographic plane 40 are not particularly limited, but it is preferable that a plurality of tomographic planes 40 be arranged at equal intervals in the optical axis direction. The position information acquisition unit 7a acquires, for example, the above-mentioned reference position SOD and the slice thicknesses d, and the range of the tomographic position numbers j as the tomographic range to be acquired. The range of the tomographic position number j is represented, for example, by the set of starting and ending numbers of consecutive tomographic position numbers. In the example of FIG. 5, for example, assuming j=−2 to j=+2, the position information acquisition unit 7a acquires each of the tomographic positions of the five tomographic planes 40 specified by each tomographic position number of j=−2, −1, 0, +1, and +2.

Figure 17:
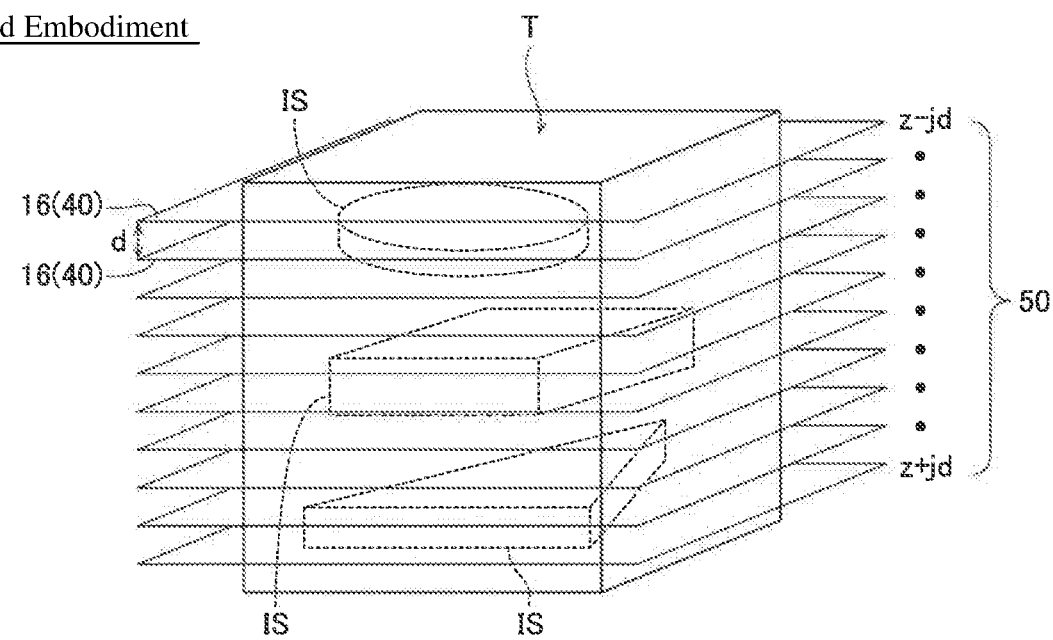
FIG. 17 is a schematic diagram for explaining three-dimensional data of a subject according to a third embodiment.

In the third embodiment, the image processing unit 6 is configured to acquire the phase-contrast image 16 in each tomographic plane 40 and generate three-dimensional data 50 of the subject T shown in FIG. 17 based on the resulting phase-contrast image 16.

The method of acquiring the phase-contrast image 16 in each tomographic plane 40 is the same as that in the above-mentioned first embodiment or second embodiment. The image processing unit 6 generates the phase-contrast image 16 in each tomographic plane 40 by repeating the coordinate transformation by changing the tomographic position (z+jd) by the number of the plurality of tomographic positions (z+jd). Note that for a plurality of X-ray images 10 and a plurality of phase information 12, it is sufficient to acquire once.

As shown in FIG. 17, the image processing unit 6 arranges the phase-contrast images 16 of the resulting respective tomographic planes 40 in the optical axis direction in tomographic position number order to generate three-dimensional data 50 of the subject T. The three-dimensional data 50 includes a plurality of phase-contrast images 16 of each tomographic plane 40 and the position information (tomographic position) of each tomographic plane 40 in the optical axis direction. The three-dimensional data 50 may be an array of respective phase-contrast images 16 simply arranged according to the tomographic positions (z−jd to z+jd) in the optical axis direction. The smaller the set value of the slice thickness d, the smaller the distance between the cross-sections and the more precise three-dimensional data can be acquired. The image processing unit 6 may reconstruct the phase-contrast image 16 of each tomographic plane 40 as stereoscopic three-dimensional data 50 complementing the region between each cross-section, rather than an array of tomographic images, by performing known approximate computations and complementary processing. This makes it possible to depict the three-dimensional distribution of the internal structure IS distributed in the optical axis direction in the subject T.

Figure 18:
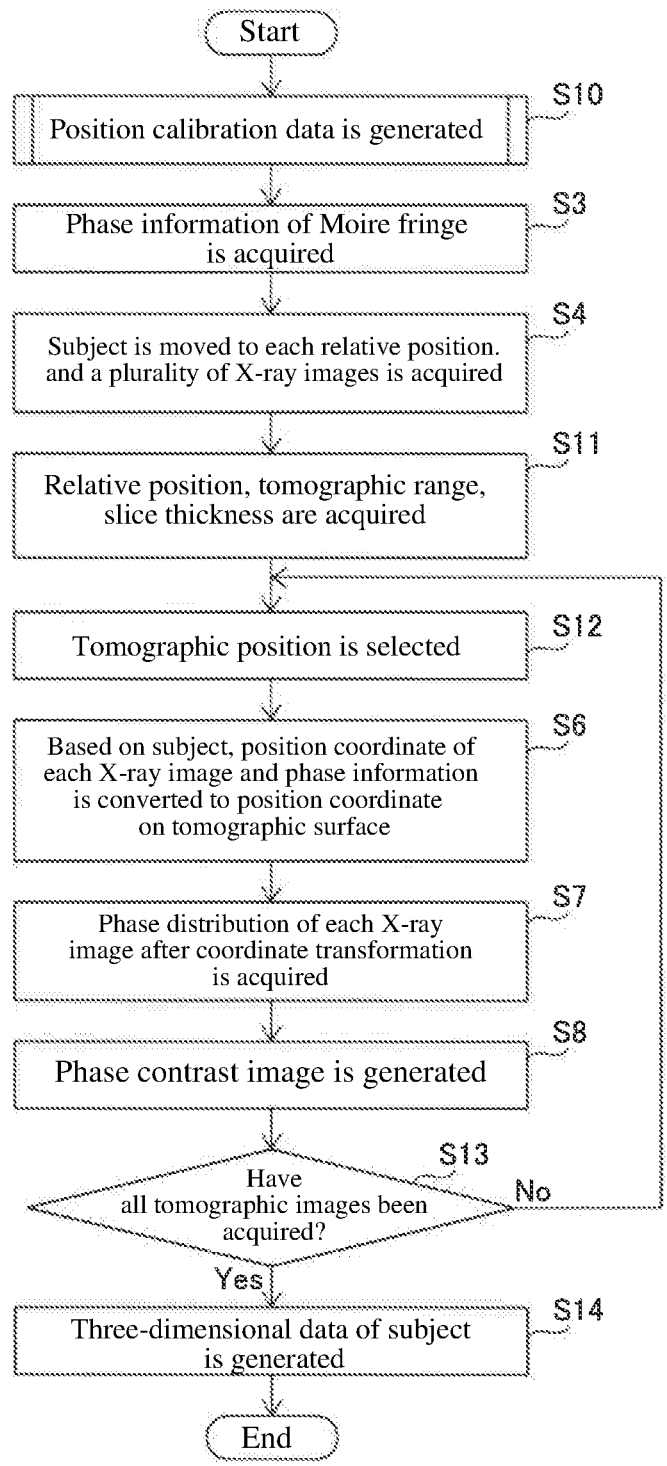
FIG. 18 is a flowchart for explaining generation processing of three-dimensional data by an X-ray imaging device according to a third embodiment.

Next, referring to FIG. 18, a flow of processing for generating three-dimensional data 50 in the X-ray imaging device 300 according to the third embodiment will be described. The same Step number is assigned to the same processing as that of the above-described first embodiment, and the descriptions thereof will be omitted.

In Step S10, the image processing unit 6 generates position calibration data 45. Step S10 is a summary of Step S1 and Step S2 in FIG. 15, and the explanation thereof is omitted. The image processing unit 6 acquires the phase information 12 of the Moire fringe 30 in Step S3 and acquires the X-ray image 10 in a plurality of relative positions in Step S4.

In Step S11, the position information acquisition unit 7a acquires the reference position SOD, the slice thickness d, and the slice thickness tomographic range (the region of the tomographic position number j). In Step S12, the image processing unit 6 selects a tomographic position (tomographic position number j) to be imaged from the acquired tomographic range. Then, the image processing unit 6 performs the coordinate transformation to the position coordinate of the tomographic plane 40 specified at the selected tomographic position (z+jd) in Steps S6 to S8 and acquires the phase distribution to generate the phase-contrast image 16 of the tomographic plane 40 specified by the selected tomographic position (tomographic position number j).

In Step S13, the image processing unit 6 determines whether or not all tomographic images included in the tomographic range acquired in Step S11 have been generated. When all tomographic images have not been generated, the image processing unit 6 returns to Step S12 and selects the next tomographic position (tomographic position number j) to be imaged from the acquired tomographic range to generate the phase-contrast image 16 of the selected tomographic plane 40. When all tomographic images included in the tomographic range are generated, the image processing unit 6 proceeds to Step S14 and generates the three-dimensional data 50 of the subject T based on the phase-contrast image 16 of each tomographic plane 40.

The rest of the configuration of the third embodiment is the same as that of the first and second embodiments.

Effects of Third Embodiment

In the third embodiment, the following effects can be obtained.

In the third embodiment, as described above, the position information acquisition unit 7a is provided for acquiring the tomographic positions (z+jd) of a plurality of tomographic planes 40 shifted in the optical axis direction, and the image processing unit 6 is configured to acquire the phase-contrast image 16 in each tomographic plane 40 and generate the three-dimensional data 50 of the subject T based on the acquired phase-contrast image 16. With this, from the plurality of tomographic images, it is possible to acquire the three-dimensional data 50 depicting the distribution of the internal structure in the subject T in the optical axis direction. Further, since blurring of each image can be suppressed for each tomographic image constituting the three-dimensional data 50, the three-dimensional structure in the subject T can be grasped more precisely.

The other effects of the third embodiment are the same as those of the above-described first and second embodiments.

Fourth Embodiment

Next, referring to FIG. 19 to FIG. 22, an X-ray imaging device 400 according to a fourth embodiment will be described. Unlike the first to third embodiments in which the phase-contrast image 16 is generated based on the X-ray image 10 acquired by detecting the X-rays that have passed through the first grating 2, in the fourth embodiment, an example is shown in which the phase-contrast image 23 is generated by the first image 21 acquired in the first detection region R1 for detecting the X-rays arriving through the first grating 2, and the absorption image 24 is generated by the second image 22 acquired in the second detection region R2 for detecting the X-rays arrived without passing through the first grating 2. The same component as that of the first to third embodiment is denoted by the same reference symbol, and the descriptions thereof will be omitted.

(Configuration of X-Ray Imaging Device)

Figure 19:
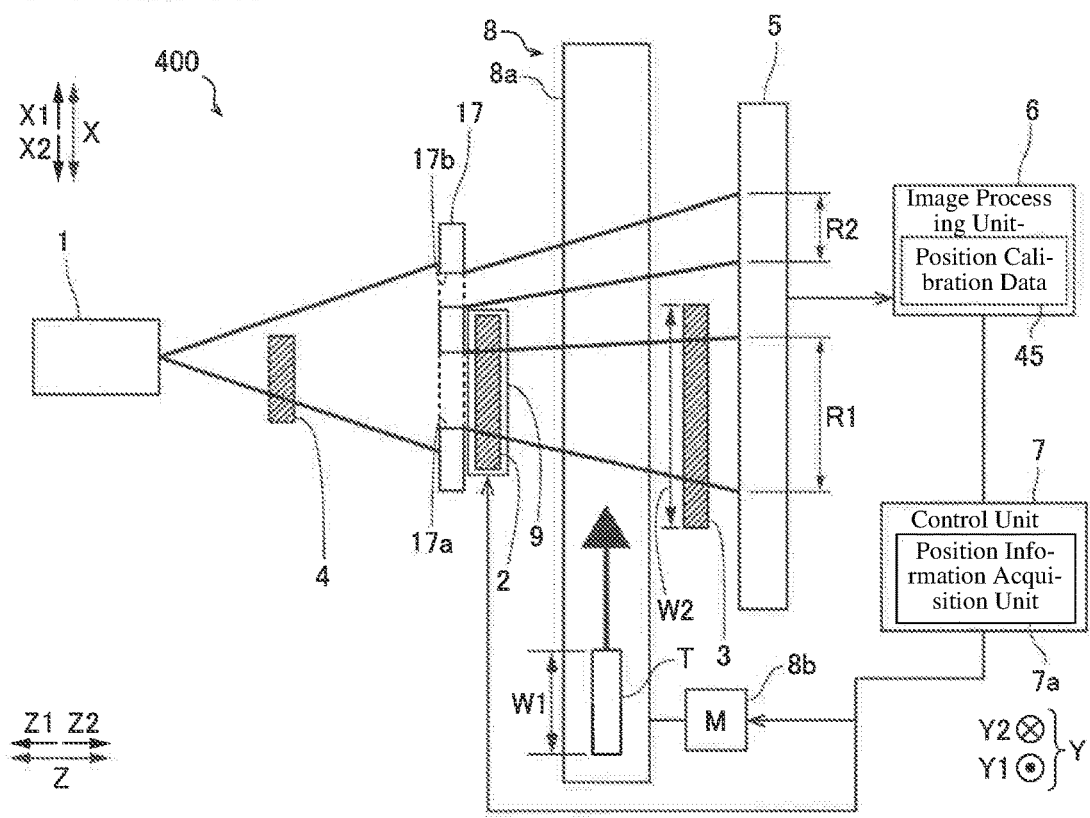
FIG. 19 is a schematic diagram showing a configuration of an X-ray imaging device according to a fourth embodiment.

As shown in FIG. 19, in the fourth embodiment, the detector 5 includes the first detection region R1 for detecting the X-rays arrived by passing through the first grating 2 and a second detection region R2 for detecting the X-rays arrived without passing through the first grating 2. The first detection region R1 and the second detection region R2 are arranged side by side in the predetermined direction (X-direction) along which the subject T and the imaging system C S are relatively moved by the moving mechanism 8. The moving mechanism 8 relatively moves the imaging system CS and the subject T so that the subject T is arranged in the first detection region R1 and the second detection region R2, respectively.

The first grating 2 and the second grating 3 are arranged on the optical path of the X-rays incident on the first detection region R1. In FIG. 19, the first grating 2, the second grating 3, and the third grating 4 are arranged on the optical path of the X-rays entering the first detection region R1. The first detection region R1 has a size in which at least one period D4 of the Moire fringe 30 (see FIG. 4) is reflected.

In the example of FIG. 19, a grating (first grating 2, second grating 3, and third grating 4) is not arranged on the optical path of the X-rays entering the second detection region R2. Since the second detection region R2 is a region for imaging the absorption image 24 (see FIG. 20) without intervening a grating, the size of the second detection region R2 in the X-direction may be smaller than the size of one period D4 of the Moire fringe 30.

In the third embodiment, the X-ray imaging device 300 includes a collimator 17. The collimator 17 is arranged between the third grating 4 and the first grating 2. The collimator 17 is constituted by a shielding member for shielding X-rays and is formed with collimator holes 17a and 17b which are configured to be freely opened and closed. The collimator hole 17a can adjust the irradiation range (range of the first detection region R1) of the X-rays that have passed through the first grating 2 and are emitted to the detector 5 among the X-rays emitted from the X-ray source 1. The collimator hole 17b can adjust the range of the X-rays (the range of the second detection region R2) emitted to the detector 5 without passing through the first grating 2.

The image processing unit 6 is configured to generate the phase-contrast image 23 (see FIG. 20) based on the plurality of first images 21 (see FIG. 20) acquired in the first detection region R1 and generate the absorption image 24 (see FIG. 20) of the subject T based on the plurality of second images 22 (see FIG. 20) acquired in the second detection region R2.

Figure 20:
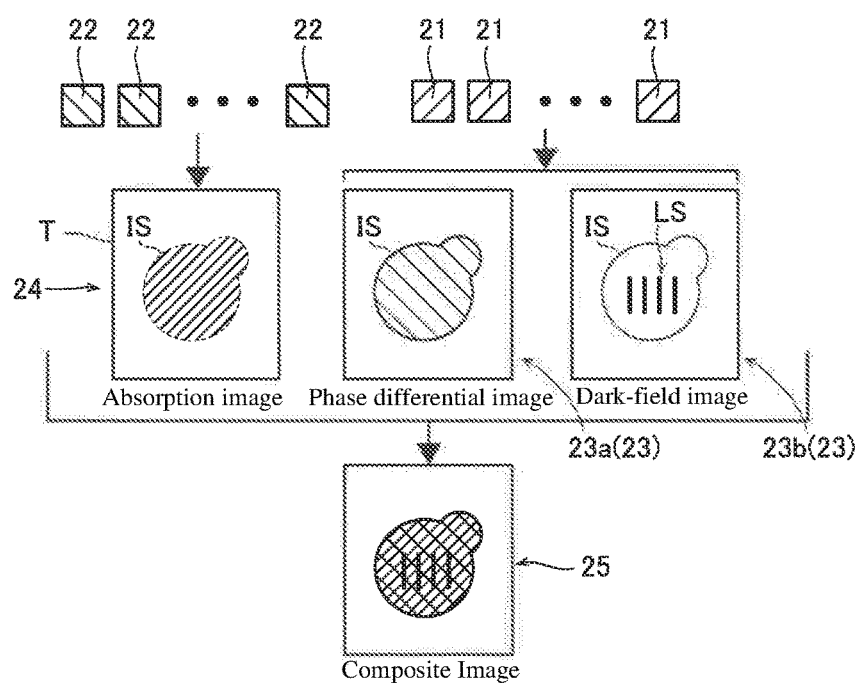
FIG. 20 is a diagram for explaining a composite image in which a phase-contrast image and an absorption image are composed.

In the third embodiment, the image processing unit 6 acquires a plurality of first images 21 captured by imaging the subject T at a plurality of relative positions from the first detection region R1. The image processing unit 6 generates the phase-contrast image 23 (the phase differential image 23a and the dark-field image 23b) in the tomographic plane 40 by acquiring the phase distribution of the plurality of first images 21 in the tomographic plane 40, as shown in FIG. 20. The method of generating the phase differential image 23a and the dark-field image 23b is similar to that in the above-described first embodiment.

The image processing unit 6 acquires a plurality of second images 22 captured by imaging the subject T at a plurality of relative positions from the second detection region R2. The image processing unit 6 generates the absorption image 24 in the tomographic plane 40 by acquiring the distribution of the signal strength of the plurality of second images 22 in the tomographic plane 40. The generation of the absorption image 24 in the tomographic plane 40 is performed by performing the coordinate transformation of the position coordinates of the plurality of second images 22 into a stationary coordinate system with reference to the subject T on the tomographic plane 40 based on the acquired tomographic position (z+jd) and adding the pixel value of each second image 22 after the coordinate transformation for each pixel.

As shown in FIG. 20, the image processing unit 6 is configured to generate a composite image 25 in which the phase-contrast image 23 and the absorption image 24 in the same tomographic plane 40 are composed. The image processing unit 6 generates the phase-contrast image 23 (the phase differential image 23a and the dark-field image 23b) based on the first images 21 and the absorption image 24 based on the second images 22 in the same tomographic plane 40. Then, the image processing unit 6 generates the composite image 25 by performing a coordinate transformation so that the position of the subject T in the phase-contrast image 23 and that in the absorption image 24 coincide and composing them.

Figure 21:
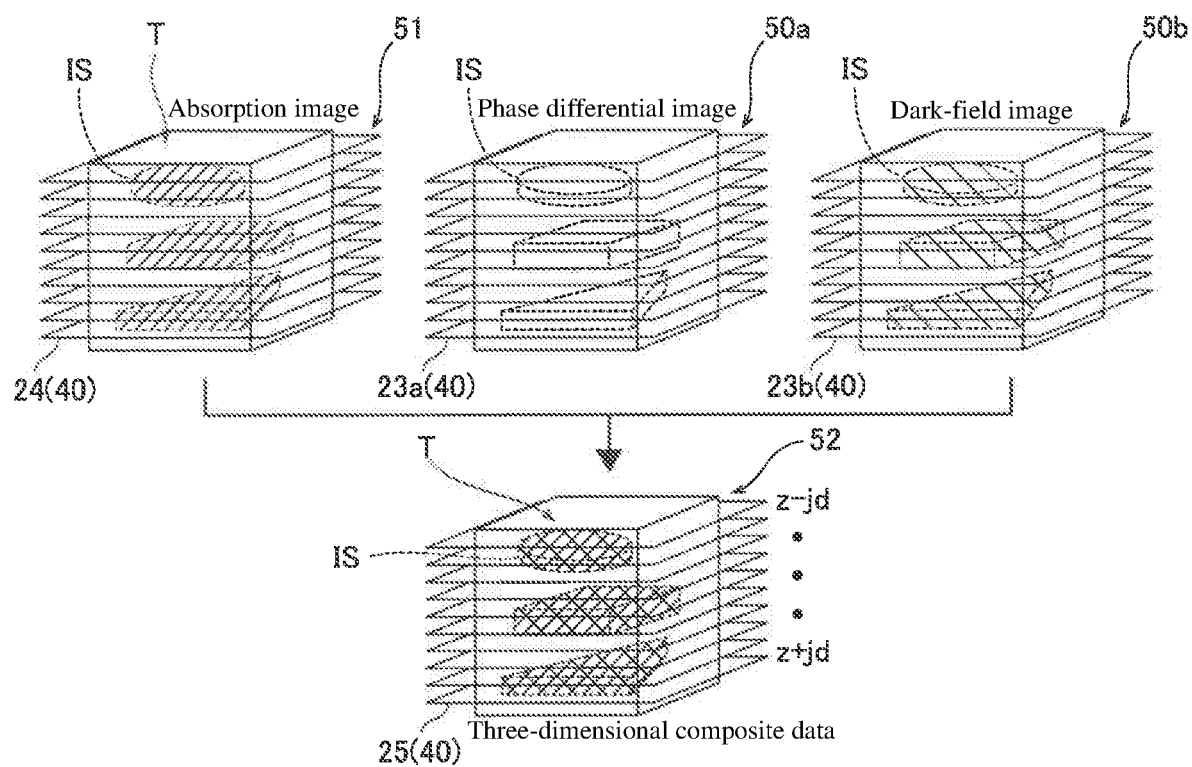
FIG. 21 is a diagram for explaining three-dimensional composite data.

As shown in FIG. 21, even in the fourth embodiment, the position information acquisition unit 7a (see FIG. 19) can acquire the tomographic positions (range of the tomographic position number j) of the plurality of tomographic planes 40 shifted in the optical axis direction. The image processing unit 6 acquires the phase-contrast images 23 and the absorption images 24 at the respective tomographic planes 40 to generate the three-dimensional data 50a and 50b of the phase-contrast images 23 and the three-dimensional data 51 of the absorption images 24. Then, the three-dimensional composite data 52 in which the respective three-dimensional data are composed is generated. Note that the three-dimensional data 50a is three-dimensional data of the phase differential image 23a, and the three-dimensional data 50b is three-dimensional data of the dark-field image 23b.

The method for generating each three-dimensional data 50 is the same as that of the third embodiment. The image processing unit 6 generates the three-dimensional composite data 52 by performing a coordinate transformation so that the position of the subject T in each of three-dimensional data 50a and 50b of the phase-contrast image 23 and that in the three-dimensional data 51 of the absorption image 24 coincide.

Figure 22:
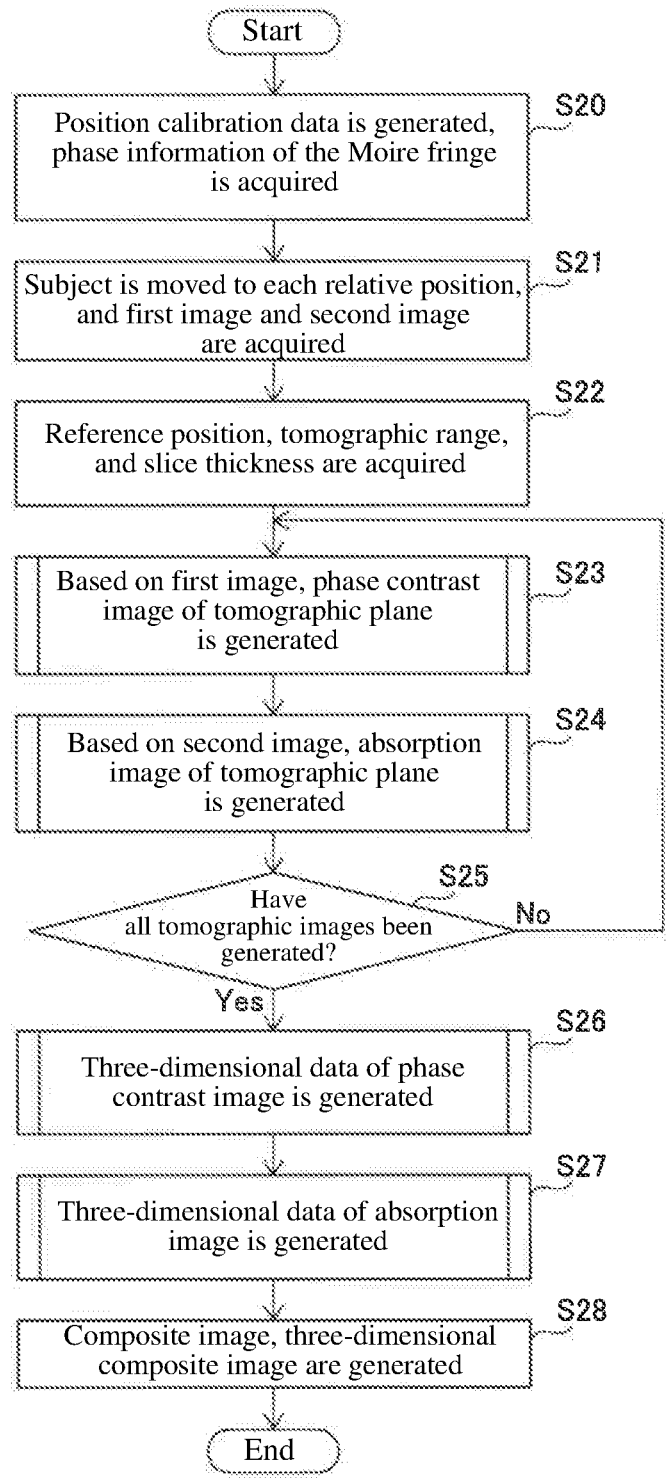
FIG. 22 is a flowchart for explaining generation processing of three-dimensional composite data by the X-ray imaging device according to the fourth embodiment.

Next, referring to FIG. 22, the flow of processing for generating the three-dimensional composite data 52 in the X-ray imaging device 400 according to the fourth embodiment will be described.

In Step S20, the image processing unit 6 acquires the position calibration data 45 and the phase information 12 of the Moire fringe 30. The acquisition processing of the phase information 12 of the position calibration data 45 and the Moire fringe 30 in Step S10 is the same as the processing of Step S1 to Step S3 in FIG. 15.

In Step S21, the image processing unit 6 acquires a plurality of first images 21 and a plurality of second images 22 captured while moving the subject T. Thereafter, in Step S22, the position information acquisition unit 7a acquires the reference position SOD, the slice thickness d, and the slice thickness tomographic range (the range of the tomographic position number j). In Step S23, the image processing unit 6 generates the phase-contrast image 23 based on the plurality of first images 21. In Step S24, the image processing unit 6 generates the absorption images 24 based on the plurality of second images 22. In Step S25, the image processing unit 6 determines whether or not all tomographic images included in the tomographic range acquired in Step S22 have been generated. When all tomographic images have not been generated, the image processing unit 6 returns to Step S23, selects the next tomographic position to be imaged from the acquired tomographic range, and generates the phase-contrast images 23 and the absorption images 24 of the selected tomographic plane 40.

When all tomographic images included in the tomographic range are generated, the image processing unit 6 proceeds to Step S26, and generates the three-dimensional data 50a and 50b of the phase-contrast image 23 based on the phase-contrast image 23 of each tomographic plane 40. In Step S27, the image processing unit 6 generates the three-dimensional data 51 of the absorption image 24 based on the absorption image 24 of each tomographic plane 40.

Thereafter, in Step S27, the image processing unit 6 generates three-dimensional composite data 52 in which three-dimensional data 50a and 50b of the phase-contrast images 23 and the three-dimensional data 51 of the absorption images 24 are composed. In this case, each tomographic image included in the three-dimensional composite data 52 is generated as a composite image 25 in which the phase-contrast images 23 and the absorption images 24 in the same tomographic plane 40 are composed.

The rest of the configuration of the fourth embodiment is the same as that of the first to third embodiments.

Effects of Fourth Embodiment

In this fourth embodiment, the following effects can be obtained.

In the fourth embodiment, as described above, the detector 5 is provided with a first detection region R1 for detecting the X-rays reached by passing through the first grating 2 and the second detection region R2 for detecting the X-rays reached without passing through the first grating 2. The moving mechanism 8 is configured to relatively move the imaging system CS and the subject T so that the subject T is arranged in the first detection region R1 and the second detection region R2, respectively, and the image processing unit 6 is configured to generate the phase-contrast image 23 based on the plurality of first images 21 acquired in the first detection region R1 and generate the absorption image 24 of the subject T based on the plurality of the second image 22 acquired in the second detection region R2. With this, not only the phase-contrast image 23 captured by interposing the grating but also the absorption image 24 captured without interposing the grating can be acquired. Since the X-rays reaching the second detection region R 2 reaches the detector 5 without passing through the grating, it is possible to suppress the attenuation of the X-rays by the grating, in particular, the attenuation of the X-rays on the low-energy side. As a result, the contrast of the absorption image 24 generated by the X-rays reaching the second detection region R2 can be improved, as compared with the contrast of the absorption image 24 generated by the X-rays reaching the first detection region R1.

In the fourth embodiment, as described above, the image processing unit 6 is configured to generate the composite image 25 in which the phase-contrast image 23 and the absorption image 24 in the same tomographic plane 40 are composed. With this, it is possible to acquire the composite image 25 in which the high-contrast absorption image 24 generated by the X-rays detected in the second detection region R2 and the phase-contrast image 23 in the same tomographic plane 40 are composed. Consequently, by setting the tomographic image of the particular tomographic plane 40, while suppressing blurring of the image, it is possible to acquire a high-contrast tomographic image (composite image 25) including the absorption (attenuation) distribution and the phase distribution information in the tomographic plane 40.

Further, in the fourth embodiment, as described above, the image processing unit 6 is configured to generate the three-dimensional data 50a and 50b of the phase-contrast image 23 and the three-dimensional data 51 of the absorption image 24 to generate the three-dimensional composite data 52 in which the respective three-dimensional data are composed. With this, from the phase-contrast image 23 and the absorption image 24 in each of the tomographic plane 40 and the absorption image of the plurality of tomographic planes, it is possible to acquire the three-dimensional data 50 depicting the distribution of the internal structure IS in the subject T in the optical axis direction in the subject T. The phase-contrast image 23 is suitable for depicting the border portion or the fine structural change that causes refraction or scattering of X-rays in the internal structure IS of the subject T, and the absorption image 24 is suitable for depicting the solid portion that causes attenuation of X-rays. For example, in FIG. 20, the phase differential image 23a is likely to cause a contrast at the border of the internal structure IS, and the dark-field image 23b is likely to cause a contrast in the microstructure such as a linear portion LS present in the internal structure IS. Therefore, by acquiring the three-dimensional composite data 52 in which the depictable portion of the phase-contrast image 23 and that of the absorption image 24 are compose, it is possible to more accurately depict the three-dimensional structure in the subject T.

Note that the other effects of the fourth embodiment are the same as those of the first to third embodiments.

Modifications

It should be understood that the embodiments disclosed here are examples in all respects and are not restrictive. The scope of the present invention is indicated by the appended claims rather than by the descriptions of the above-described embodiments and includes all modifications (changes) within the meanings and the ranges equivalent to the scope of the claims.

For example, in the above-described first to fourth embodiments, an example is shown in which the grating moving mechanism 9 moves the first grating 2, but the present invention is not limited thereto. A grating to be moved may be any grating.

In the above-described first to fourth embodiments, a configuration example is shown in which the X-ray imaging device 100 (200, 300, 400) is provided with the third grating 4, but the present invention is not limited thereto. In cases where the coherence of the X-rays emitted from the X-ray source 1 is sufficiently high so that it is possible to form a self-image of the first grating 2, it is not necessary to provide the third grating 4.

In the above-described first to fourth embodiments, a configuration example is shown in which the subject T (marker M) is moved between the first grating 2 and the second grating 3, but the present invention is not limited thereto. For example, it may be configured to move the subject T (marker M) between the third grating 4 and the first grating 2.

In the above-described first to fourth embodiments, an example is shown in which the position calibration data 45 is generated as an approximate expression (the above-described Expression (5) or the above-described Expression (8)) based on the command value and the movement amount, but the present invention is not limited thereto. In cases where the position of the pixel in each X-ray image 10 can be acquired, the position calibration data 45 may be generated in any way. Further, instead of generating the position calibration data 45 by the position calibration image 13, the transformation coefficient p1 may be a known constant.

In the above-described first to fourth embodiments, an example is shown in which the absorption image, the phase differential image, and the dark-field image are generated as the phase-contrast image 16(23), but the present invention is not limited thereto. As the phase-contrast image 16(23), any one or two of the absorption images, the phase differential image, and the dark-field image may be generated.

In the fourth embodiment, an example is shown in which the composite image 25 in which the phase differential image 23a and the dark-field image 23b are composed is generated, but the present invention is not limited thereto. For example, one of the phase differential image 23a and the dark-field image 23b may be composed with the absorption image 24 to generate the composite image 25. The same applies to the three-dimensional composite data 52.

In the above-described first to fourth embodiments, the size W1 of the subject T to be imaged in the X-direction is not particularly limited. The size W1 of the subject T in the X-direction may be larger than the width W2 of the second grating 3 or the width of the first detection region R1 and that of the second detection region R2 in the X-direction. In such cases, by composing a part of the image of the subject T captured while moving the subject T to be connected in the X-direction, it is possible to generate an image in which the entire subject T is reflected.

In the above-described first to fourth embodiments, an example is shown in which the moving mechanism 8 moves the subject T to perform imaging, but the present invention is not limited thereto. For example, the moving mechanism 8 may be configured to relatively move the subject T and the imaging system CS by moving the imaging system CS with the subject T fixed. The moving mechanism 8 may move any one of the subject T (marker M) and the imaging system CS. In cases where the moving mechanism 8 moves the imaging system CS, the moving mechanism 8 may be configured to move the grating moving mechanism 9 and the collimator 17.

Further, in the above-described first to fourth embodiments, an example is shown in which the position away from the focal point to the center position of the subject T by the distance SOD is taken as the reference position, but the present invention is not limited thereto. The reference position can be set to any position in the optical axis direction. For example, the reference position may be the detection surface position SID, and the tomographic position may be the deviation from the detection surface position SID. As described above, it is preferable that the reference position be a position (position in the optical axis direction) of the marker M when generating the position calibration data 45 to ensure the position accuracy.

Further, in the above-described first to fourth embodiments, an example is shown in which the tomographic position is the deviation from the reference position, but the present invention is not limited thereto. In the present invention, without setting the reference position, the tomographic position of each tomographic plane 40 may be defined, for example, as the distance (position in the optical axis direction) from the focal point of the X-ray source 1.

DESCRIPTION OF SYMBOLS

1: X-ray source
2: First grating
3: Second grating
4: Third grating
5: Detector
6: Image processing unit
7: Control unit
7a: Position information acquisition unit
8: Moving mechanism
10, 14: X-ray image
13: Position calibration image
16, 23: Phase-contrast image
16a: Absorption image (phase-contrast image)
16b, 23a: Phase differential image (phase-contrast image)
16c, 23b: Dark-field image (phase-contrast image)
21: First image
22: Second image
24: Absorption image
25: Composite image
32, 34: Intensity signal curve (phase distribution)
40: Tomographic plane
45: Position calibration data
50, 50a, 50b, 51: Three-dimensional data
52: Three-dimensional composite data
100, 200, 300, 400: X-ray imaging device
CS: Imaging system
M: Marker
R1: First detection region
R2: Second detection region
SOD: Reference position
T: subject
X-direction (predetermined direction)
Z-direction (optical axis direction)

The invention claimed is:

1. An X-ray imaging device comprising:
an X-ray source;
a detector configured to detect X-rays emitted from the X-ray source;
a plurality of gratings arranged between the X-ray source and the detector, the plurality of gratings including a first grating configured to be irradiated with the X-rays from the X-ray source and a second grating configured to be irradiated with X-rays that have passed through the first grating;
a moving mechanism configured to relatively move an imaging system and a subject in a predetermined direction intersecting with an optical axis direction of the X-rays, the imaging system including the X-ray source, the detector, and the plurality of gratings;
a position information acquisition unit configured to acquire a tomographic position of a tomographic plane to be imaged in the optical axis direction; and
an image processing unit configured to acquire a phase distribution in the tomographic plane based on 1) a plurality of X-ray images acquired by imaging the subject at a plurality of relative positions between the imaging system and the subject in the predetermined direction and on 2) the acquired tomographic position, thereby generating a phase-contrast image in the tomographic plan.

2. The X-ray imaging device as recited in claim 1,
wherein the image processing unit is configured to perform a coordinate transformation for special coordinates in each of the X-ray images into ones defined in a translated coordinate system on the tomographic plane, based on 1) the relative position at the time of capturing each X-ray image and 2) the acquired tomographic position, thereby acquiring a phase distribution in the tomographic plane based on pixel values of each of the X-ray images after the coordinate defined from the transformed coordinate system.

3. The X-ray imaging device as recited in claim 1,
wherein the position information acquisition unit acquires a deviation of the tomographic position relative to a reference position in the optical axis direction, and
wherein the image processing unit is configured to acquire a phase distribution in the tomographic plane based on a deviation between the reference position and the tomographic position relative to the reference position in the optical axis direction and the relative position between the imaging system and the subject in the predetermined direction.

4. The X-ray imaging device as recited in claim 3,
wherein the image processing unit is configured to:
generate position calibration data that associate a movement amount by the moving mechanism with a change amount of the relative position in the X-ray image, based on a plurality of position calibration images captured by imaging a marker arranged at the reference position in the optical axis direction at a plurality of relative positions in the predetermined directions; and
acquire a phase distribution in the tomographic plane using the position calibration data acquired at the reference position.

5. The X-ray imaging device as recited in claim 4,
wherein the moving mechanism is configured to relatively move the imaging system and the subject to the same relative position as each relative position between the imaging system and the marker at the time of generating the position calibration data when imaging the subject.

6. The X-ray imaging device as recited in claim 1,
wherein the position information acquisition unit acquires the tomographic positions of the plurality of tomographic planes shifted in the optical axis direction, and
wherein the image processing unit is configured to acquire the phase-contrast image in each tomographic plane and generate three-dimensional data of the subject based on the acquired phase-contrast image.

7. The X-ray imaging device as recited in claim 1,
wherein the moving mechanism is configured to continuously and relatively move the imaging system and the subject when imaging the subject, and
wherein the image processing unit is configured to generate the phase-contrast image based on each of the X-ray images acquired continuously.

8. The X-ray imaging device as recited in claim 1,
wherein the moving mechanism is configured to move the subject to the plurality of relative positions by repeatedly performing a relative movement of the imaging system and the subject and stopping of the relative movement thereof when imaging the subject, and
wherein the image processing unit is configured to generate the phase-contrast image based on the respective X-ray images acquired at the plurality of relative positions.

9. The X-ray imaging device as recited in claim 1,
wherein the moving mechanism is configured to move the subject with respect to the imaging system in the predetermined direction.

10. The X-ray imaging device as recited in claim 1,
wherein the detector includes a first detection region for detecting X-rays arrived by passing through the first grating and a second detection region for detecting X-rays arrived without passing through the first grating,
wherein the moving mechanism relatively moves the imaging system and the subject so that the subject is arranged in the first detection region and the second detection region, respectively, and
wherein the image processing unit is configured to generate the phase-contrast image based on a plurality of first images captured in the first detection region and generate an absorption image of the subject based on a plurality of second images captured in the second detection region.

11. The X-ray imaging device as recited in claim 10,
wherein the image processing unit is configured to generate a composite image in which the phase-contrast image and the absorption image in the same tomographic plane are composed.

12. The X-ray imaging device as recited in claim 11,
wherein the position information acquisition unit acquires the tomographic positions of the plurality of tomographic planes shifted in the optical axis direction, and
wherein the image processing unit is configured to acquire the phase-contrast image and the absorption image in each tomographic plane to generate three-dimensional data of the phase-contrast image and three-dimensional data of the absorption image and generate three-dimensional composite data in which the respective three-dimensional data is composed.

13. The X-ray imaging device as recited in claim 1,
wherein the plurality of gratings further includes a third grating arranged between the X-ray source and the first grating.

* * * * *